(12) United States Patent  (10) Patent No.: US 6,632,963 B1
Bernardon  (45) Date of Patent: Oct. 14, 2003

(54) BICYCLIC AROMATIC COMPOUNDS AND PHARMACEUTICAL/COSMETIC COMPOSITIONS COMPRISED THEREOF

(75) Inventor: Jean-Michel Bernardon, Le Rouret (FR)

(73) Assignee: Galderma Research & Development S.N.C., Valbonne (FR)

( * ) Notice: Subject to any disclaimer, the term of this patent is extended or adjusted under 35 U.S.C. 154(b) by 0 days.

(21) Appl. No.: 09/277,953

(22) Filed: Mar. 29, 1999

Related U.S. Application Data

(63) Continuation of application No. 09/277,953, filed on Mar. 29, 1999.

(30) Foreign Application Priority Data

Mar. 31, 1998 (FR) .............................. 98 03976

(51) Int. Cl.$^7$ .............................. C07C 62/06
(52) U.S. Cl. .................. 562/466; 560/102; 549/78; 549/79; 549/497; 549/499; 548/560; 548/564; 568/630; 568/632
(58) Field of Search ......................... 560/102; 562/466; 568/630, 632; 548/560, 564; 549/78, 79, 497, 499

(56) References Cited

U.S. PATENT DOCUMENTS 6,001,885 A 12/1999 Vega et al.

FOREIGN PATENT DOCUMENTS

FR EP0826368 3/1998
WO 97/33881 9/1997

*Primary Examiner*—Paul J. Killos
(74) *Attorney, Agent, or Firm*—Burns, Doane, Swecker & Mathis, L.L.P.

(57) ABSTRACT

Novel pharmaceutically/cosmetically-active bicyclic aromatic compounds have the structural formula (I):

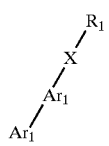

(I)

in which $Ar_1$ is a radical having one of the structural formulae (a)–(c):

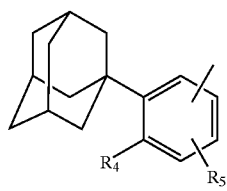

(a)

-continued

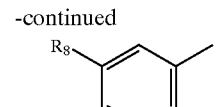
(b)

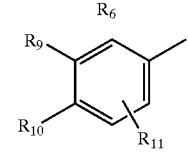

(c)

$Ar_2$ is a radical having one of the following formulae (d)–(h):

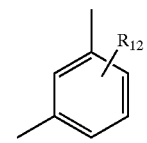

(d)

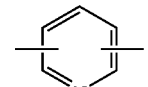

(e)

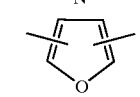

(f)

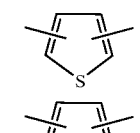

(g)

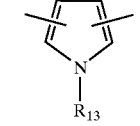

(h)

and X is a radical having one of the following formulae (i)–(l):

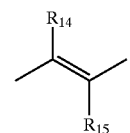

(i)

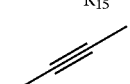

(j)

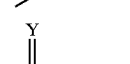

(k)

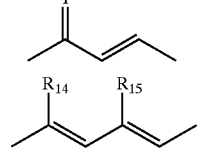

(l)

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

56 Claims, 1 Drawing Sheet

BICYCLIC AROMATIC COMPOUNDS AND PHARMACEUTICAL/COSMETIC COMPOSITIONS COMPRISED THEREOF

CROSS-REFERENCE TO PRIORITY APPLICATION

This application is a continuation of U.S. application Ser. No. 09/277,953, filed on Mar. 29, 1999, which claims priority of International Application No. 98-03976, filed in France on Mar. 31, 1998.

The application claims priority under 35 U.S.C. §119 of FR-98/03976, filed Mar. 31, 1998, hereby expressly incorporated by reference.

BACKGROUND OF THE INVENTION

Technical Field of the Invention

The present invention relates to novel biaromatic compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention have pronounced activity in the fields of cell differentiation and proliferation, and are particularly useful in the topical and systemic treatment of dermatological conditions associated with a keratinization disorder, dermatological (or other) conditions including an inflammatory and/or immunoallergic component, and dermal or epidermal proliferations, whether benign or malignant. The subject compounds can also be used for the treatment of degenerative diseases of connective tissue, to combat aging of the skin, whether photoinduced or chronological aging, and to treat cicatrization disorders. They are also useful for ophthalmological applications, especially for the treatment of corneopathies.

The compounds according to the invention can also be formulated into cosmetic compositions for body and hair hygiene.

Briefly, the bicyclic aromatic compounds according to this invention have the following structural formula (I):

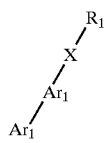
(I)

in which $R_1$ is (i) the radical —$CH_3$, (ii) a radical —$CH_2OR_2$, or (iii) a radical —CO—$R_3$, wherein $R_2$ and $R_3$ are as defined below; $Ar_1$ is a radical selected from among those of the following formulae (a)–(c):

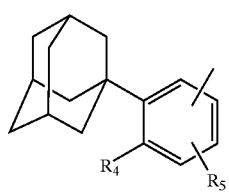
(a)

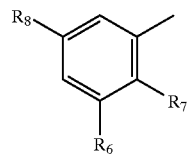
(b)

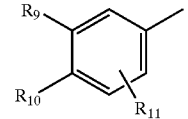
(c)

wherein $R_4$, $R_5$, $R_6$, $R_7$, $R_8$, $R_9$, $R_{10}$ and $R_{11}$ are as defined below; $Ar_2$ is a radical selected from among those of the following formulae (d)–(h):

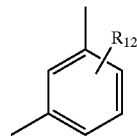
(d)

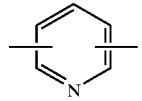
(e)

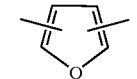
(f)

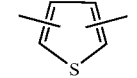
(g)

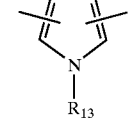
(h)

wherein $R_{12}$ and $R_{13}$ are as defined below; X is a radical selected from among those of the following formulae (i)–(l):

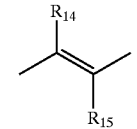
(i)

(j)

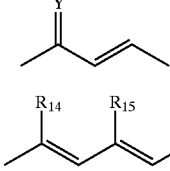
(k)

(l)

wherein $R_{14}$, $R_{15}$ and Y are as defined below; $R_2$ is a hydrogen atom, a lower alkyl radical or a radical —CO—

$R_{16}$, wherein $R_{16}$ is as defined below; $R_3$ is a hydrogen atom, a lower alkyl radical, a radical of the formula:

wherein R' and R" are as defined below, or a radical —$OR_{17}$, wherein $R_{17}$ is as defined below; $R_4$ is a hydrogen atom, a polyether radical, a lower alkyl radical, or a radical —$OR_{18}$, wherein $R_{18}$ is as defined below; $R_5$ is a hydrogen atom, a lower alkyl radical, a polyether radical, or a radical —$OR_{19}$, wherein $R_{19}$ is as defined below; $R_6$ is a tert-butyl radical; $R_7$ is a lower alkyl radical, a polyether radical, or a radical —$OR_{20}$, wherein $R_{20}$ is as defined below, with the proviso that $R_6$ and $R_7$ may together form, with the carbon atoms from which they depend, a 6-membered ring optionally substituted with at least one methyl group and/or optionally interrupted by an oxygen or sulfur atom; $R_8$ is a tert-butyl, adamantyl, aryl or aralkyl radical; $R_9$ and $R_{10}$ together form, with the carbon atoms from which they depend, a 5- or 6-membered ring optionally substituted with at least one methyl group and/or optionally interrupted by an oxygen or sulfur atom; $R_{11}$ is a hydrogen atom, a lower alkyl radical having from 1 to 9 carbon atoms, a hydroxyl radical, an alkoxy radical, a polyether radical or a radical —$OR_{21}$, wherein $R_{21}$ is as defined below; $R_{12}$ is a hydrogen atom, a hydroxyl radical, an alkoxy radical, a polyether radical or a radical —$OR_{22}$, wherein $R_{22}$ is as defined below; $R_{13}$ is a hydrogen atom, a lower alkyl radical, or a radical —$COR_{23}$, wherein $R_{23}$ is as defined below; $R_{14}$ and $R_{15}$, which may be identical or different, are each a hydrogen atom, or a lower alkyl radical; Y is an oxygen atom or a $CH_2$ radical; $R_{16}$ is a lower alkyl radical; $R_{17}$ is a hydrogen atom, a linear or branched alkyl radical having from 1 to 20 carbon atoms, an alkenyl radical, a mono- or polyhydroxyalkyl radical, an optionally substituted aryl or aralkyl radical or a sugar residue; R' and R", which may be identical or different, are each a hydrogen atom, a lower alkyl radical, a mono- or polyhydroxyalkyl radical, an optionally substituted aryl radical or an amino acid residue, with the proviso that R' and R" may together form, with the nitrogen atom from which they depend, a nitrogenous heterocycle; $R_{18}$, $R_{19}$ and $R_{20}$, which may be identical or different, are each a hydrogen atom, a lower alkyl radical, an alkenyl radical, a mono- or polyhydroxyalkyl radical, an aryl radical, an optionally substituted aralkyl radical or a radical —$(CH_2)_n$—$R_{24}$, wherein n and $R_{24}$ are as defined below; $R_{21}$ and $R_{22}$, which may be identical or different, are each an alkenyl radical, a mono- or polyhydroxyalkyl radical, an aryl radical, an optionally substituted aralkyl radical, or a radical —$(CH_2)_n$—$R_{24}$, wherein n and $R_{24}$ are as defined below; $R_{23}$ is a lower alkyl radical; $R_{24}$ is a heterocycle, a monohydroxyalkyl radical, a thiol radical optionally substituted with a lower alkyl radical, an amino radical optionally substituted with at least one lower alkyl radical, a radical —$COOR_{25}$, or a radical —$CON(R_{26})R_{27}$, wherein $R_{25}$, $R_{26}$ and $R_{27}$ are as defined below; $R_{25}$ is a hydrogen atom or a lower alkyl radical; $R_{26}$ and $R_{27}$, which may be identical or different, are each a hydrogen atom, a lower alkyl radical, or an optionally substituted aryl radical, with the proviso that $R_{26}$ and $R_{27}$ may together form, with the nitrogen atom from which they depend, a nitrogenous heterocycle; n is an integer such that $2 \leq n \leq 9$; with the further provisos that, when $Ar_1$ is the radical of formula (c) and X is a radical of formulae (i) or (j), then $R_{11}$ is the radical —$OR_{21}$ or a polyether radical, or when $Ar_2$ is the radical of formula (d), then $R_{12}$ is the radical —$OR_{22}$ or a polyether radical, and the compounds of formula (I) do not include those wherein $R_{11}$ is a methoxymethoxy radical in an ortho position relative to the substituent $Ar_2$ when $Ar_1$ is the radical of formula (c), X is the radical of formula (i), $R_{12}$ is hydrogen and $R_1$ is the radical —$COR_3$ wherein $R_3$ is the radical —$OR_{17}$ and $R_{17}$ is a hydrogen atom, and those wherein $R_{12}$ is a methoxymethoxy radical in an ortho- or para-position relative to the substituent $Ar_1$ when $Ar_1$ is the radical of formula (c), X is the radical of formula (i), $R_{11}$ is a methyl radical in an ortho-position relative to $Ar_2$, and $R_1$ is the radical —$COR_3$ wherein $R_3$ is the radical —$OR_{17}$ and $R_{17}$ is a hydrogen atom.

This invention also features the salts of the compounds of formula (I) when $R_1$ represents a carboxylic acid function, and the geometrical and optical isomers of said compounds of formula (I).

When the compounds according to the invention are in the form of salts, they are preferably salts of an alkali or alkaline earth metal, or, alternatively, of zinc or of an organic amine.

BRIEF DESCRIPTION OF THE DRAWINGS

The FIGURE of Drawing sets forth reaction schemes/mechanisms illustrating representative syntheses for the preparation of the bicyclic aromatic compounds according to the present invention.

DETAILED DESCRIPTION OF BEST MODE AND SPECIFIC/PREFERRED EMBODIMENTS OF THE INVENTION

Figure 1:
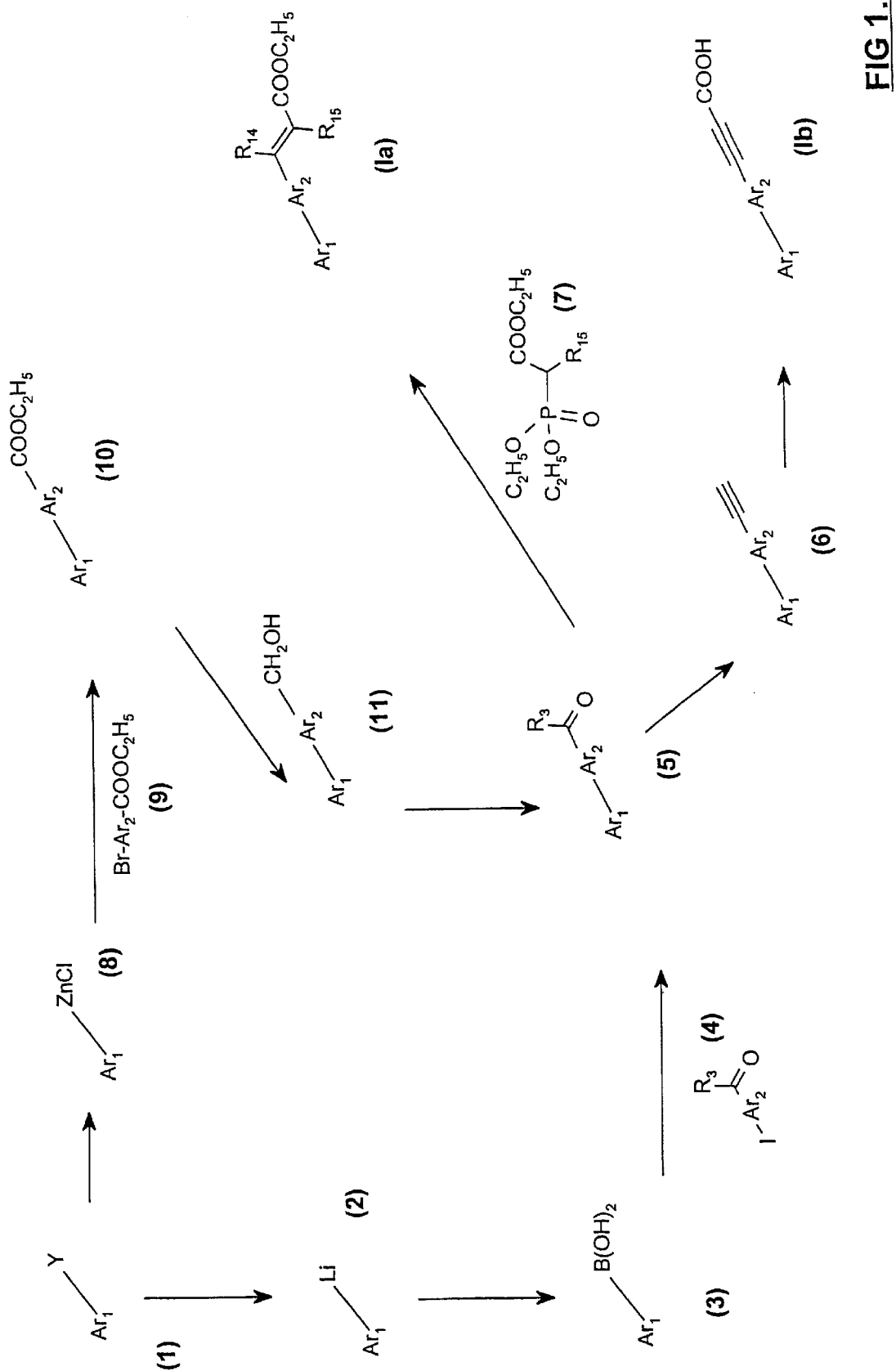

More particularly according to the present invention, by the term "lower alkyl radical" is intended an alkyl radical having from 1 to 12, preferably from 1 to 9, carbon atoms, advantageously the methyl, ethyl, propyl, isopropyl, butyl, tert-butyl, pentyl, hexyl, heptyl, nonyl, decyl and dodecyl radicals.

By the expression "linear or branched alkyl radical having from 1 to 20 carbon atoms" are particularly intended the methyl, ethyl, propyl, isopropyl, tert-butyl, octyl and 2-ethylhexyl radicals.

By the term "alkoxy radical" is intended an alkoxy radical preferably having from 1 to 9 carbon atoms, in particular the methoxy, propyloxy, pentyloxy and heptyloxy radicals.

By the term "monohydroxyalkyl" or "polyhydroxyalkyl" radical is intended a radical having from 1 to 6 carbon atoms and from 1 to 5 hydroxyl groups. Among such monohydroxyalkyl radicals, preferred are those having 2 or 3 carbon atoms, in particular a 2-hydroxyethyl, 2-hydroxypropyl or 3-hydroxypropyl radical. Among such polyhydroxyalkyl radicals, preferred are those having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals, or the pentaerythritol residue.

By the term "aryl radical" is preferably intended a phenyl radical optionally substituted with at least one halogen atom, lower alkyl radical, hydroxyl group, alkoxy radical, nitro function, polyether radical, or an amino function optionally protected with an acetyl group or optionally substituted with at least one lower alkyl radical.

By the term "aralkyl radical" is preferably intended a benzyl or phenethyl radical optionally substituted with at least one halogen atom, lower alkyl radical, hydroxyl group, alkoxy radical, nitro function, a polyether radical or an amino function optionally protected with an acetyl group or optionally substituted with at least one lower alkyl radical.

By the term "alkenyl radical" is preferably intended an alkenyl radical having from 2 to 5 carbon atoms and containing one or more sites of ethylenic unsaturation, such as, more particularly, the allyl radical.

By the term "polyether radical" is intended a radical having from 1 to 6 carbon atoms and from 1 to 3 oxygen or sulfur atoms, such as the methoxymethyl ether, methoxyethoxymethyl ether or methylthiomethyl ether radicals.

By "sugar residues" are preferably intended those derived, for example, from glucose, galactose, mannose or glucuronic acid.

By "amino acid residue" is preferably intended one derived, for example, from at least one of the 20 amino acids of L or D configuration constituting mammalian proteins. More particularly intended are the residues derived from lysine, glycine or aspartic acid.

By "heterocycle" is preferably intended piperidino, morpholino, pyrrolidino or piperazino, optionally substituted in the 4-position with a $C_1$–$C_6$ alkyl radical or with a mono- or polyhydroxyalkyl radical as defined above.

Among the compounds of formula (I) according to the present invention, particularly representative are the following:

- 3-(3',5'-Di-tert-butyl-2'-methoxy-3-biphenylyl)acrylic acid;
- 3-(2'-Benzyloxy-3',5'-di-tert-butyl-6-hydroxy-3-biphenylyl)acrylic acid;
- 3-(3',5'-Di-tert-butyl-6-hydroxy-2'-pentyloxy-3-biphenylyl)acrylic acid;
- 3-(3',5'-Di-tert-butyl-6-hydroxy-2'-methoxy-3-biphenylyl)acrylic acid;
- 3-[3-(3-Benzyloxy-5,5,8,8-tetramethyl-5,6,7,8-tetrahydro-2-naphthyl)-4-methoxymethoxyphenyl]acrylic acid;
- 3-[3-(3-Benzyloxy-5,5,8,8-tetramethyl-5,6,7,8-tetrahydro-2-naphthyl)-4-hydroxyphenyl]acrylic acid;
- [4-Methoxymethoxy-3-(3,5,5,8,8-pentamethyl-5,6,7,8-tetrahydro-2-naphthyl)phenyl]propynoic acid;
- 3-[3-(3-Propyloxy-5,5,8,8-tetramethyl-5,6,7,8-tetrahydro-2-naphthyl)-4-methoxymethoxyphenyl]acrylic acid;
- 3-[3-(3-Pentyloxy-5,5,8,8-tetramethyl-5,6,7,8-tetrahydro-2-naphthyl)-4-methoxymethoxyphenyl]acrylic acid;
- 3-(5'-Adamantan-1-yl-4'-methoxy-2'-methyl-3-biphenylyl)acrylic acid;
- 3-(5'-Adamantan-1-yl-6-hydroxy-4'-methoxy-2'-methyl-3-biphenylyl)acrylic acid;
- 3-(5'-Adamantan-1-yl-4'-methoxy-6-methoxymethoxy-2'-methyl-3-biphenylyl)acrylic acid;
- 3-{4-Methoxy-3-[3-(3-methoxybenzyloxy)-5,5,8,8-tetramethyl-5,6,7,8-tetrahydro-2-naphthyl]phenyl}acrylic acid;
- 3-{4-Methoxy-3-[3-(4-methoxybenzyloxy)-5,5,8,8-tetramethyl-5,6,7,8-tetrahydro-2-naphthyl]phenyl}acrylic acid;
- 3-{3-[3-(6-Hydroxyhexyloxy)-5,5,8,8-tetramethyl-5,6,7,8-tetrahydro-2-naphthyl]-4-methoxyphenyl}acrylic acid;
- 3-{3-[3-(7-Hydroxyheptyloxy)-5,5,8,8-tetramethyl-5,6,7,8-tetrahydro-2-naphthyl]-4-methoxyphenyl}acrylic acid;
- 3-{3-[3-(5-Hydroxypentyloxy)-5,5,8,8-tetramethyl-5,6,7,8-tetrahydro-2-naphthyl]-4-methoxyphenyl}acrylic acid;
- 3-{3-[3-(3-Hydroxypropyloxy)-5,5,8,8-tetramethyl-5,6,7,8-tetrahydro-2-naphthyl]-4-methoxyphenyl}acrylic acid;
- 3-[3-(1-Benzyloxy-5,5,8,8-tetramethyl-5,6,7,8-tetrahydro-2-naphthyl)phenyl]acrylic acid;
- 3-(3'-Adamantan-1-yl-4'-hydroxy-3-biphenylyl)acrylic acid;
- 5-[4-Methoxy-3-(5,5,8,8-tetramethyl-5,6,7,8-tetrahydro-2-naphthyl)phenyl]-3-methylpenta-2,4-dienoic acid;
- 5-[4-Methoxymethoxy-3-(5,5,8,8-tetramethyl-5,6,7,8-tetrahydro-2-naphthyl)phenyl]-3-methylpenta-2,4-dienoic acid;
- 5-[4-Hydroxy-3-(5,5,8,8-tetramethyl-5,6,7,8-tetrahydro-2-naphthyl)phenyl]-3-methylpenta-2,4-dienoic acid;
- 3-{3-[3-(5-Tert-butoxycarbonylpentyloxy)-5,5,8,8-tetramethyl-5,6,7,8-tetrahydro-2-naphthyl]-4-methoxyphenyl}acrylic acid;
- 3-{3-[3-(7-Tert-butoxycarbonylheptyloxy)-5,5,8,8-tetramethyl-5,6,7,8-tetrahydro-2-naphthyl]-4-methoxyphenyl}acrylic acid;
- 3-{3-[3-(7-Carboxyheptyloxy)-5,5,8,8-tetramethyl-5,6,7,8-tetrahydro-2-naphthyl]-4-methoxyphenyl}acrylic acid;
- 3-{3-[3-(5-Carboxypentyloxy)-5,5,8,8-tetramethyl-5,6,7,8-tetrahydro-2-naphthyl]-4-methoxyphenyl}acrylic acid;
- 3-{3-[3-(5-Carbamoylpentyloxy)-5,5,8,8-tetramethyl-5,6,7,8-tetrahydro-2-naphthyl]-4-methoxyphenyl}acrylic acid;
- 3-{3-[3-(7-Carbamoylheptyloxy)-5,5,8,8-tetramethyl-5,6,7,8-tetrahydro-2-naphthyl]-4-methoxyphenyl}acrylic acid;
- 3-{4-Methoxy-3-[5,5,8,8-tetramethyl-3-(2-morpholin-4-ylethoxy)-5,6,7,8-tetrahydro-2-naphthyl]phenyl}acrylic acid;
- 3-{4-Methoxy-3-[5,5,8,8-tetramethyl-3-(2-piperidin-1-ylethoxy)-5,6,7,8-tetrahydro-2-naphthyl]phenyl}acrylic acid;
- 3-{4-Methoxy-3-[3-(2-methoxymethoxybenzyloxy)-5,5,8,8-tetramethyl-5,6,7,8-tetrahydro-2-naphthyl]phenyl}acrylic acid;
- 3-{4-Methoxy-3-[3-(3-methoxymethoxybenzyloxy)-5,5,8,8-tetramethyl-5,6,7,8-tetrahydro-2-naphthyl]phenyl}acrylic acid;
- 3-{4-Methoxy-3-[3-(4-methoxymethoxybenzyloxy)-5,5,8,8-tetramethyl-5,6,7,8-tetrahydro-2-naphthyl]phenyl}acrylic acid;
- 3-{4-Methoxy-3-[3-(3-hydroxybenzyloxy)-5,5,8,8-tetramethyl-5,6,7,8-tetrahydro-2-naphthyl]phenyl}acrylic acid;
- 3-[4-Fluoro-3-(3,5,5,8,8-pentamethyl-5,6,7,8-tetrahydro-2-naphthyl)phenyl]acrylic acid;
- 3-{4-Hydroxy-3-[3-(3-methoxybenzyloxy)-5,5,8,8-tetramethyl-5,6,7,8-tetrahydro-2-naphthyl]phenyl}acrylic acid;
- 3-{4-Hydroxy-3-[3-(4-methoxybenzyloxy)-5,5,8,8-tetramethyl-5,6,7,8-tetrahydro-2-naphthyl]phenyl}acrylic acid;
- 3-{4-Hydroxy-3-[3-(4-fluorobenzyloxy)-5,5,8,8-tetramethyl-5,6,7,8-tetrahydro-2-naphthyl]phenyl}acrylic acid;
- 3-{4-Hydroxy-3-[3-(4-chlorobenzyloxy)-5,5,8,8-tetramethyl-5,6,7,8-tetrahydro-2-naphthyl]phenyl}acrylic acid;

3-[4-Hydroxy-3-(3-methoxymethoxy-5,5,8,8-tetramethyl-5,6,7,8-tetrahydro-2-naphthyl)phenyl]acrylic acid;

3-(3',5'-Di-tert-butyl-6-hydroxy-2'-propyloxy-3-biphenylyl)acrylic acid;

3-(3',5'-Di-tert-butyl-6-hydroxy-2'-butyloxy-3-biphenylyl)acrylic acid;

3-(2'-Butoxy-3',5'-di-tert-butyl-6-methoxy-3-biphenylyl)acrylic acid;

3-(3'5'-Di-tert-butyl-6-methoxy-2'-propoxy-3-biphenylyl)acrylic acid;

3-[4-Hydroxy-3-(5,5,8,8-tetramethyl-4-propoxy-5,6,7,8-tetrahydro-2-naphthyl)phenyl]acrylic acid;

3-[3-(3-Benzyloxy-5,5,8,8-tetramethyl-5,6,7,8-tetrahydro-2-naphthyl)-4-methoxyphenyl]acrylic acid;

Ethyl 3-[3-(3-benzyloxy-5,5,8,8-tetramethyl-5,6,7,8-tetrahydro-2-naphthyl)-4-methoxyphenyl]acrylate;

3-Methyl-5-[3-(3,5,5,8,8-pentamethyl-5,6,7,8-tetrahydro-2-naphthyl)phenyl]penta-2,4-dienoic acid;

3-[3-(3-Benzyloxy-5,5,8,8-tetramethyl-5,6,7,8-tetrahydro-2-naphthyl)-4-methoxyphenyl]prop-2-en-1-ol;

3-[3-(3-Benzyloxy-5,5,8,8-tetramethyl-5,6,7,8-tetrahydro-2-naphthyl)-4-methoxyphenyl]propenal;

N-Ethyl 3-[3-(3-benzyloxy-5,5,8,8-tetramethyl-5,6,7,8-tetrahydro-2-naphthyl)-4-methoxyphenyl]-acrylamide;

3-[3-(3-Benzyloxy-5,5,8,8-tetramethyl-5,6,7,8-tetrahydro-2-naphthyl)-4-methoxyphenyl]-1-morpholin-4-yl-propenone;

N-(4-Hydroxyphenyl)-3-[3-(3-benzyloxy-5,5,8,8-tetramethyl-5,6,7,8-tetrahydro-2-naphthyl)-4-methoxyphenyl]acrylamide;

5-(5'-Adamantan-1-yl-4'-methoxy-2'methyl-3-biphenylyl)-3-methylpenta-2,4-dienoic acid;

5-[4-Methoxymethoxy-3-(3,5,5,8,8-pentamethyl-5,6,7,8-tetrahydro-2-naphthyl)phenyl]-3-methylpenta-2,4-dienoic acid;

5-[4-Hydroxy-3-(3,5,5,8,8-pentamethyl-5,6,7,8-tetrahydro-2-naphthyl)phenyl]-3-methylpenta-2,4-dienoic acid;

4-[3-(3,5,5,8,8-Pentamethyl-5,6,7,8-tetrahydro-2-naphthyl)phenyl]penta-2,4-dienoic acid;

5-(3',5'-Di-tert-butyl-2'-methoxy-3-biphenylyl)-3-methylpenta-2,4-dienoic acid;

5-(3',5'-Di-tert-butyl-2'-propoxy-3-biphenylyl)-3-methylpenta-2,4-dienoic acid;

5-(2'-Butoxy-3',5'-di-tert-butyl-3-biphenylyl)-3-methylpenta-2,4-dienoic acid;

5-(2'-Butoxy-3',5'-di-tert-butyl-6-hydroxy-3-biphenylyl)-3-methylpenta-2,4-dienoic acid;

5-(3',5'-Di-tert-butyl-6-hydroxy-2'-propoxy-3-biphenylyl)-3-methylpenta-2,4-dienoic acid;

5-(3',5'-Di-tert-butyl-6-hydroxy-2'-methoxy-3-biphenylyl)-3-methylpenta-2,4-dienoic acid.

According to the present invention, the compounds of formula (I) which are more particularly preferred are those for which at least one, and preferably all, of the following conditions are satisfied:

$R_1$ is a radical —CO—$R_3$;

$Ar_2$ is a radical of formulae (d) or (e);

$R_{11}$ is a radical —O—$R_{21}$;

$R_7$ is a radical —O—$R_{20}$.

The present invention also features processes for preparing the compounds of formula (I), in particular according to the reaction scheme illustrated in the FIGURE of Drawing.

The compounds of formula (Ia) can be obtained (FIGURE of Drawing) from aldehyde or ketone derivatives (5), according to a Horner-type reaction with a lithium or sodium derivative of a phosphonate (7), it being possible for the carbonyl compounds (5) to be obtained either by a coupling reaction between a boronic acid (3) and a halo derivative (4) (this reaction is carried out in the presence of a palladium catalyst, for example tetrakis(triphenylphosphine)-palladium under the conditions described by N. Miyaura et al., *Synthetic Communications*, 11(7), 513–519 (1981); the boronic acid derivative (3) can be obtained, for example, from the halo derivative (1) by conversion into the lithium derivative (2) and then reaction with trimethyl borate and hydrolysis), or by a coupling reaction between a zinc derivative (8) and a halo ester derivative (9) in the presence of a catalyst, for example a palladium or nickel derivative (NiCl$_2$dppe), followed by conversion of the ester function (10) into an alcohol (11) and oxidation into an aldehyde (5).

The compounds of formula (Ib) can be obtained from the acetylenic derivative (6) by reaction with n-butyllithium and then carboxylation in the presence of $CO_2$.

The acetylenic compounds (6) can be obtained either:

from the aldehyde derivatives (5) (when $R_3$ is a hydrogen atom), by reaction with carbon tetrabromide and triphenylphosphine to give a 2'2'-dibromostyrene derivative which is converted into an acetylenic derivative by a non-nucleophilic base such as n-butyllithium in an aprotic solvent such as tetrahydrofuran, or from the ketone derivatives (5) (when $R_3$ is a lower alkyl radical) by a sequence of reactions comprising treatment with a base such as lithium diisopropylamide, then with a dialkyl phosphate chloride and again with lithium diisopropylamide.

When $R_1$ is a —COOH radical, the compounds are prepared:

either by protecting $R_1$ with a protecting group of alkyl, allylic or tert-butyl type.

Conversion to the free form can be carried out:

in the case of an alkyl protecting group, using sodium hydroxide or lithium hydroxide in an alcoholic solvent such as methanol or in THF;

in the case of an allylic protecting group, using a catalyst such as certain transition metal complexes in the presence of a secondary amine such as morpholine;

in the case of a protecting group of tert-butyl type, using trimethylsilane iodide.

When $R_1$ is an alcohol function, the compounds can be obtained:

from the corresponding aldehyde derivatives by the action of an alkyl metal hydride, such as sodium borohydride, in an alcoholic solvent (for example methanol);

from the acid derivatives by reduction with lithium aluminum hydride.

When $R_1$ is an aldehyde function, the compounds can be obtained from the alcohol derivatives by oxidation in the presence of manganese oxide, pyridinium dichromate or Swern's reagent.

When $R_1$ is an amide function, the compounds can be obtained from the corresponding carboxylic derivatives by reaction with aliphatic, aromatic or heterocyclic amines either via an acid chloride or in the presence of dicyclohexylcarbodiimide or carbonyldiimidazole.

Certain of the subject compounds bind to the RXR receptors, some having agonist activity, others having antagonist activity. The preferred compounds have antagonist activity.

The binding and transactivation properties as RXR-receptor agonists can be determined by methods known in the art, such as, for example: Levin et al., *Nature*, 355, 359–61 (1992); Allenby et al., *Proc. Natl. Acad. Sci.*, 90, 30–4 (1993).

The RXR-agonist activity can also be determined by the test described in French patent application No. 95/07301, filed Jun. 19, 1995 by the assignee hereof. This test comprises the following steps: (i) a sufficient amount of a compound which is an active ligand for at least one receptor of the superfamily of steroidal/thyroid nuclear receptors other than a ligand specific for the RXR receptors and which can heterodimerize with the RXRs, such as an RAR-agonist molecule, is applied topically to an area of the skin of a mammal, (ii) a molecule capable of having RXR-agonist activity is administered systemically or topically to this same area of the skin of the mammal before, during or after step (i), and (iii) the response on the part of the mammal's skin thus treated is evaluated. Thus, the response to topical application to a mammal's ear of an RAR-agonist molecule which corresponds to an increase in the thickness of this ear can be increased by the systemic or topical administration of an RXR-receptor agonist molecule.

The RXRα-antagonist activity can be evaluated in the transactivation test by determination of the dose ($IC_{50}$) which gives 50% inhibition of the transactivating activity of an RXRα-selective agonist: 6-[1-(3,5,5,8,8-pentamethyl-5,6,7,8-tetrahydro-2-naphthyl)cyclopropyl]nicotinic acid (CD 3127) according to the following procedure:

HeLa cells are co-transfected with an expression vector coding for RXRα (p565-RXRα) and a reporter plasmid containing the response element ½ CRBP II cloned upstream of the thymidine kinase heterologous promoter and of the chloramphenicolm-acetyl-transferase (CAT) reporter gene. Eighteen hours after co-transfection, the cells are treated with a fixed concentration of CD 3127 and increasing concentrations of the molecule to be evaluated. After treatment for twenty-four hours, the CAT activity is assayed by ELISA. The fixed concentration of CD3127 used is $10^{-8}$M and corresponds to its $EC_{50}$.

The compounds according to the invention are particularly well suited in the following fields of therapy:

(1) for treating dermatological conditions associated with a keratinization disorder related to differentiation and on proliferation, in particular for treating common acne, comedones, polymorphonuclear leukocytes, rosacea, nodulocystic acne, acne conglobata, senile acne and secondary acnes such as solar, medication-related or occupational acne;

(2) for treating other types of keratinization disorders, in particular ichthyosis, ichthyosiform states, Darier's disease, palmoplantar keratoderma, leucoplasias and leucoplasiform states, and cutaneous or mucous (buccal) lichen;

(3) for treating other dermatological conditions associated with a keratinization disorder manifesting an inflammatory and/or immunoallergic component and, in particular, all forms of psoriasis, whether cutaneous, mucous or ungual psoriasis and even psoriatic rheumatism, or, alternatively, cutaneous atopy, such as eczema or respiratory atopy, or gingival hypertrophy; the compounds can also be used for treating inflammatory conditions not exhibiting keratinization disorder;

(4) for treating all dermal or epidermal proliferations, whether benign or malignant and whether or not of viral origin or otherwise, such as common warts, flat warts and verruciform epidermodysplasia, oral or florid papillomatoses and the proliferations which can be induced by ultraviolet radiation, in particular in the case of basocellular and spinocellular epithelioma;

(5) for treating other dermatological disorders such as bullosis and collagen diseases;

(6) for treating certain ophthalmological disorders, in particular corneopathies;

(7) for repairing or combating aging of the skin, whether photoinduced or chronological, or for reducing actinic keratoses and pigmentations, or any pathologies associated with chronological or actinic aging;

(8) for preventing or curing the stigmata of epidermal and/or dermal atrophy induced by local or systemic corticosteroids, or any other form of cutaneous atrophy;

(9) for preventing or treating cicatrization disorders or for preventing or repairing stretch marks, or, alternatively, for promoting cicatrization;

(10) for combating disorders of sebaceous functioning, such as the hyperseborrhoea of acne or simple seborrhoea;

(11) for the treatment or prevention of cancerous or precancerous states;

(12) for the treatment of inflammatory conditions such as arthritis;

(13) for the treatment of any general or skin affliction of viral origin;

(14) for the prevention or treatment of alopecia;

(15) for the treatment of dermatological or general conditions including an immunological component;

(16) for the treatment of conditions of the cardiovascular system such as arteriosclerosis, hypertension, non-insulin-dependent diabetes and obesity;

(17) for the treatment of skin disorders due to an exposure to U.V. radiation.

In the therapeutic fields indicated above, the compounds according to the invention may advantageously be administered in combination with other compounds exhibiting retinoid-type activity, with D vitamins or derivatives thereof, with corticosteroids, with anti-free-radical agents, with α-hydroxy or α-keto acids or derivatives thereof, or, alternatively, with ion-channel blockers. By the expression "D vitamins or derivatives thereof" are intended, for example, vitamin $D_2$ or $D_3$ derivatives and in particular 1,25-dihydroxyvitamin $D_3$. By "anti-free-radical agents" are intended, for example, α-tocopherol, superoxide dismutase, ubiquinol or certain metal-chelating agents. By the expression "α-hydroxy or α-keto acids or derivatives thereof" are intended, for example, lactic, malic, citric, glycolic, mandelic, tartaric, glyceric or ascorbic acid or the salts, amides or esters thereof. Lastly, by the term "ion-channel blockers" are intended, for example, Minoxidil (2,4-diamino-6-piperidinopyrimidine 3-oxide) and derivatives thereof.

The present invention thus also features medicinal compositions containing at least one compound of formula (I), one of the optical or geometrical isomers thereof, or one of the salts or other derivatives thereof.

The pharmaceutical/therapeutic compositions of this invention, intended especially for the treatment of the aforesaid disease states comprise a carrier, diluent or vehicle which is pharmaceutically acceptable and compatible with the mode of administration selected for the given composition, at least one compound of formula (I), one of the optical or geometrical isomers thereof, or one of the salts, etc., thereof.

The compounds according to the invention can be administered systemically, enterally, parenterally, topically or ocularly.

For enteral administration, the medicinal/pharmaceutical compositions may be in the form of tablets, gelatin capsules, sugar-coated tablets, syrups, suspensions, solutions, elixirs, powders, granules, emulsions, microspheres or nanospheres or polymeric or lipid vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for the treatment of the skin and the mucosae and may be in the form of ointments, creams, milks, salves, powders, pommades, impregnated pads, solutions, gels, sprays, lotions or suspensions. They may also be in the form of microspheres or nanospheres or polymeric or lipid vesicles or polymeric patches and hydrogels which permit controlled release. These topical-route compositions may either be in anhydrous form or in aqueous form, depending on the clinical indication.

For ocular administration, they are mainly eyedrops.

These compositions for topical or ocular application contain at least one compound of formula (I) as defined above, or one of the optical or geometrical isomers thereof, or one of the salts or other derivatives thereof, at a concentration preferably ranging from 0.001% to 5% by weight relative to the total weight of the composition.

The compounds of formula (I) according to the invention also find application in the cosmetic field, in particular for body and hair hygiene and especially for treating skin types with a tendency towards acne, for promoting the regrowth of the hair, for combating hair loss, for combating the greasy appearance of the skin or the hair, for protection against the harmful effects of the sun or for the treatment of physiologically dry skin types, and for preventing and/or combating photoinduced or chronological aging.

For cosmetic applications, the compounds according to the invention can moreover be employed advantageously in combination with other compounds of retinoid-type activity, with D vitamins or derivatives thereof, with corticosteroids, with anti-free-radical agents, with α-hydroxy or α-keto acids or derivatives thereof, or alternatively with ion-channel blockers, all of these various active agents being as defined above.

The present invention therefore also features cosmetic compositions comprising a cosmetically acceptable support (vehicle, diluent or carrier) which is suitable for topical application, at least one compound of formula (I) as defined above or one of the optical or geometrical isomers thereof, or one of the salts or other derivatives thereof. Such cosmetic compositions are advantageously in the form of a cream, a milk, a lotion, a gel, microspheres or nanospheres or polymeric or lipid vesicles, a soap or a shampoo.

The concentration of the compounds of formula (I) in the cosmetic compositions according to the invention advantageously ranged from 0.001% to 3% by weight relative to the total weight of the composition.

The medicinal and cosmetic compositions of the present invention can also contain inert additives and adjuvants, or even pharmacodynamically or cosmetically active additives and adjuvants, or combinations of these additives and adjuvants, in particular: wetting agents; depigmenting agents such as hydroquinone, azelaic acid, caffeic acid or kojic acid; emollients; moisturizing agents such as glycerol, PEG 400, thiamorpholinone and derivatives thereof, or urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolinones; agents for promoting the regrowth of the hair, such as Minoxidil (2,4-diamino-6-piperidinopyrimidine 3-oxide) and derivatives thereof, Diazoxide (7-chloro-3-methyl-1,2, 4-benzothiadiazine 1,1-dioxide) and Phenytoin (5,5-diphenylimidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-triynoic acid, the esters and the amides thereof.

The compositions according to the invention may also contain flavor-enhancing agents, preservatives such as parahydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or butylhydroxytoluene.

In order to further illustrate the present invention and the advantages thereof, the following specific examples are given, it being understood that same are intended only as illustrative and in nowise limitative.

A. EXAMPLES OF SYNTHESES OF COMPOUNDS, PER SE

Example 1

Synthesis of 3-(3',5'-di-tert-Butyl-2'-methoxy-3-biphenylyl)acrylic Acid (a) Preparation of 2-Bromo-4,6-di-tert-butylanisole:

6 g (21 mmol) of 2-bromo-4,6-di-tert-butylphenol and 60 ml of DMF were introduced into a round-bottomed flask under a stream of nitrogen. 694 mg (29 mmol) of sodium hydride (80% in oil) were added portionwise and the mixture was stirred until the evolution of gas had ceased. 1.45 ml (23.2 mmol) of iodomethane was then added and the mixture was stirred at room temperature for three hours. The reaction medium was poured into ice-cold water and extracted with ethyl acetate, and the organic phase was separated out after settling had taken place, dried over magnesium sulfate and evaporated. The residue obtained was purified by chromatography from a column of silica eluted with heptane. After evaporation of the solvents, 6.1 g (98%) of the expected compound were collected in the form of a colorless oil.

$^1$H NMR (d, CDCl$_3$): 1.3 (s, 9H); 1.4 (s, 9H); 3.9 (s, 3H); 7.3 (d, J=2.3 Hz, 1H); 7.4 (d, J=2.3 Hz, 1H).

(b) Preparation of 2-Methoxy-3.5-di-tert-butylphenylboronic Acid:

6 g (20.1 mmol) of 2-bromo-4,6-di-tert-butylanisole and 50 ml of THF were introduced into a three-necked flask under a stream of nitrogen. 9.7 ml (24.1 mmol) of n-butyllithium (2.5M in hexane) were added dropwise, at −78° C., and the mixture was stirred for 15 minutes. At this same temperature, 7 ml (30.1 mmol) of triisopropyl borate were added with stirring for 2 hours. 20 ml of hydrochloric acid (1N) were added at −50° C. and the mixture was permitted to warm to room temperature. The reaction medium was extracted with ethyl ether and the organic phase was separated out after settling had taken place, dried over magnesium sulfate and evaporated. The solid obtained was triturated from heptane, filtered off and dried. 4 g (75%) of the expected boronic acid were collected, which product was used without further purification in the remainder of the synthesis to follow.

$^1$H NMR (d, CDCl$_3$): 1.3 (s, 9H); 1.4 (s, 9H); 3.8 (s, 3H); 6.0 (s, 2H); 7.5 (d, J=2.5 Hz, 1H); 7.7 (d, J=2.5 Hz, 1H).

(c) Synthesis of 3-(3',5'-di-tert-Butyl-2'-methoxy-3-biphenylyl)acrylic Acid:

2.2 g (8.3 mmol) of 2-methoxy-3,5-di-tert-butylphenylboronic acid, 942 mg (4.15 mmol) of 3-bromocinnamic acid and 70 ml of DME were introduced into a three-necked flask under a stream of nitrogen. 11.4 ml of aqueous potassium carbonate solution (2M) were added dropwise and the reaction medium was degassed. 144 mg (0.12 mmol) of tetrakistriphenylphosphinepalladium(0) were then added and the mixture was refluxed for 20 hours. Water and ethyl acetate were added to the reaction medium and this mixture was acidified to pH 1 with hydrochloric acid. The organic phase was separated out after settling had taken place, washed with water, dried over magnesium sulfate and evaporated. The residue obtained was purified by chromatography on a column of silica eluted with a mixture of heptane and ethyl acetate (75/25). After evaporation of the solvents, 990 mg (66%) of 3-(3',5'-di-tert-butyl-2'-methoxy-3-biphenylyl)acrylic acid having a melting point of 182°–3° C. were collected.

$^1$H NMR (d, DMSO): 1.1 (s, 9H); 1.2 (s, 9H); 3.0 (s, 3H); 6.4 (d, J=16 Hz, 1H); 7.0 (d, J=2.3 Hz, 1H); 7.1 (d, J=2.3 Hz, 1H); 7.3–7.6 (m, 5H).

Example 2

Synthesis of 3-(2'-Benzyloxy-di-tert-butyl-6-hydroxy-3-biphenylyl)acrylic Acid (a) Preparation of 3-Bromo-4-hydroxybenzaldehyde:

15 g (123 mmol) of 4-hydroxybenzaldehyde, 687 mg (12.3 mmol) of iron powder, 200 ml of dichloromethane and 10 ml of THF were introduced into a 500 ml three-necked flask under nitrogen atmosphere. The mixture was cooled to 0° C., 19.60 g (123 mmol) of bromine were added dropwise and this mixture was stirred at room temperature for one hour. Saturated sodium thiosulfate solution was added, the dichloromethane was evaporated off, the residue was extracted with ethyl acetate, the organic phase was separated out after settling had taken place, washed with water to neutral pH and dried over magnesium sulfate, and the solvents were evaporated off. The residue obtained was purified by chromatography on a column of silica eluted with an eluting system composed of 80% heptane and 20% dichloromethane. After evaporation of the solvents, 9.7 g (39%) of a white cottony powder having a melting point of 121°–124° C. were collected.

(b) Preparation of 3-Bromo-4-methoxymethoxybenzaldehyde:

9 g (44.7 mmol) of 3-bromo-4-hydroxy-benzaldehyde, 30 ml of THF and 30 ml of DMF were introduced into a 250 ml round-bottomed flask under a nitrogen atmosphere. 1.48 g (49.2 mmol) of 80% sodium hydride were added portionwise, the mixture was stirred for thirty minutes at room temperature and 4.32 g (52.7 mmol) of methoxymethyl chloride were added dropwise. The reaction medium was stirred for one hour at room temperature, acidified with 1N hydrochloric acid and extracted with ethyl acetate. The organic phase was separated out after settling had taken place, washed with water to neutral pH and dried over magnesium sulfate, and the solvents were evaporated off. 11.5 g (100%) of an orange-colored oil were collected.

(c) Preparation of Ethyl 3-(3-Bromo-4-methoxymethoxyphenyl)acrylate:

12 g (53 mmol) of triethyl phosphonoacetate and 50 ml of THF were introduced into a three-necked flask under a stream of nitrogen. 2.45 g (81.6 mmol) of sodium hydride (80% in oil) were added portionwise and the mixture was stirred until the evolution of gas had ceased. A solution of 10 g (40.8 mmol) of 3-bromo-4-methoxymethoxybenzaldehyde in 50 ml of THF was then added and this mixture was stirred at room temperature for one hour. The reaction medium was poured into water, acidified with hydrochloric acid and extracted with ethyl acetate, and the organic phase was separated out after settling had taken place, dried over magnesium sulfate and evaporated. The residue obtained was purified by chromatography on a column of silica eluted with a mixture of heptane and ethyl acetate (90-10). After evaporation of the solvents, 9.6 g (74%) of ethyl 3-(3-bromo-4-methoxymethoxyphenyl)acrylate having a melting point of 63°–65° C. were collected.

(d) Preparation of 2-Benzyloxy-3,5-di-tert-butylbromobenzene:

In a manner similar to that of Example 1(a), by reaction of 6 g (21 mmol) of 2-bromo-4,6-di-tert-butylphenol with 2.8 ml (23.2 mmol) of benzyl bromide, 7.4 g (94%) of the expected compound were obtained in the form of a colorless oil.

$^1$H NMR (d, CDCl$_3$): 1.3 (s, 9H); 1.4 (s, 9H); 5.1 (s, 2H); 7.25–7.45 (m, 5H); 7.55–7.6 (m, 2H).

(e) Preparation of 2-Benzyloxy-3,5-di-tert-butylphenylboronic Acid:

In a manner similar to that of Example 1(b), by reaction of 7.2 g (19.3 mmol) of 2-benzyloxy-3,5-di-tert-butylbromobenzene with 6.7 ml (29 mmol) of triisopropyl borate, 4.29 g (65%) of the expected boronic acid were obtained.

$^1$H NMR (d, CDCl$_3$): 1.35 (s, 9H); 1.45 (s, 9H); 5.1 (s, 2H); 5.9 (s, 2H); 7.3–7.55 (m, 6H); 7.7 (d, J=2.5 Hz, 1H).

(f) Preparation of Ethyl 3-(2'-Benzyloxy-3',5'-di-tert-butyl-6'-methoxymethoxy-3-biphenylyl)acrylate:

In a manner similar to that of Example 1(c), by reaction of 3.24 g (9.53 mmol) of 2-benzyloxy-3,5-di-tert-butylphenylboronic acid with 2 g (6.35 mmol) of ethyl 3-(3-bromo-4-methoxymethoxyphenyl)acrylate, 2.4 g (71%) of the expected ethyl ester were obtained.

$^1$H NMR (d, CDCl$_3$): 1.1 (t, J=7 Hz, 3H); 1.35 (s, 9H); 1.45 (s, 9H); 3.5 (s, 3H); 4.25 (q, J=7 Hz, 2H); 4.5 (s, 2H); 5.1 (s, 2H); 6.3 (d, J=16 Hz, 1H); 6.9–7.0 (m, 2H); 7.15–7.25 (m, 5H); 7.4–7.5 (m, 2H); 7.6–7.7 (m, 2H).

(g) Preparation of Ethyl 3-(2'-Benzyloxy-3',5'-di-tert-butyl-6-hydroxy-3-biphenylyl)acrylate:

2.14 g (4 mmol) of the above ethyl ester, 10 ml of THF and 10 ml of ethanol were introduced into a round-bottomed flask. 1 ml of concentrated sulfuric acid was added and the mixture was stirred at room temperature for 24 hours. The reaction medium was poured into water and extracted with ethyl acetate, and the organic phase was separated out after settling had taken place, washed with water, dried over magnesium sulfate and evaporated. The residue obtained was triturated from heptane, filtered and dried. 1.93 g (100%) of the expected compound was collected.

$^1$H NMR (d, CDCl$_3$): 1.3 (t, J=7 Hz, 3H); 1.35 (s, 9H); 1.45 (s, 9H); 4.25 (q, J=7 Hz, 2H); 4.5–4.7 (m, 2H); 6.4 (d, J=16 Hz, 1H); 7.0 (d, J=8 Hz, 1H); 7.0–7.1 (m, 2H); 7.25 (s, 1H); 7.3–7.4 (m, 3H); 7.45–7.50 (m, 2H); 7.6 (s, 1H); 7.7 (d, J=6 Hz, 1H).

(h) Synthesis of 3-(2'-Benzyloxy-3',5'-di-tert-butyl-6-hydroxy-3-biphenylyl)acrylic Acid:

1.93 g (4 mmol) of ethyl 3-(2'-benzyloxy-3',5'-di-tert-butyl-6-hydroxy-3-biphenylyl)acrylate, 20 ml of THF, 2 ml of methanol and 4 ml of sodium hydroxide solution (10N) were introduced into a round-bottomed flask. The reaction medium was refluxed for 12 hours, poured into water, acidified to pH 1 with hydrochloric acid and extracted with ethyl acetate, and the organic phase was separated out after settling had taken place, dried over magnesium sulfate and evaporated. The residue obtained was triturated from heptane, filtered and dried. 1.6 g (87%) of 3-(2'-benzyloxy-3',5'-di-tert-butyl-6-hydroxy-3-biphenylyl)acrylic acid having a melting point of 230°–1° C. was collected.

$^1$H NMR (d, CDCl$_3$): 1.3 (s, 9H); 1.5 (s, 9H); 4.6 (s, 2H); 6.3 (d, J=16 Hz, 1H); 7.0–7.1 (m, 3H); 7.2–7.3 (m, 4H); 7.4–7.5 (m, 2H); 7.6 (s, 1H); 7.7 (d, J=16 Hz, 1H); 8.1 (m, 1H).

Example 3

Synthesis of 3-(3',5'-di-tert-Butyl-6-hydroxy-2'-pentyloxy-3-biphenylyl)acrylic Acid (a) Synthesis of 3,5-di-tert-Butyl-2-pentyloxybromobenzene:

In a manner similar to that of Example 1(a), by reaction of 6 g (21 mmol) of 2-bromo-4,6-di-tert-butylphenol with 3 ml (23.2 mmol) of iodopentane, 7.3 g (98%) of the expected compound were obtained in the form of a colorless oil.

$^1$H NMR (d, CDCl$_3$): 0.9 (t, J=7 Hz, 3H); 1.35 (s, 9H); 1.45 (s, 9H); 1.3–1.5 (m, 4H); 1.8–2.0 (m, 2H); 4.0 (q, J=7 Hz, 2H); 7.3 (d, J=2.5 Hz, 1H); 7.4 (d, J=2.5 Hz, 1H).

(b) Preparation of 3,5-di-tert-Butyl-2-pentyloxyphenylboronic Acid:

In a manner similar to that of Example 1(b), by reaction of 7.26 g (20.5 mmol) of 3,5-di-tert-butyl-2-pentyloxybromobenzene with 7.1 ml (30.75 mmol) of triisopropyl borate, 6.4 g (98%) of the expected boronic acid were obtained.

$^1$H NMR (d, CDCl$_3$): 0.9 (t, J=7 Hz, 3H); 1.2–1.5 (m, 4H); 1.35 (s, 9H); 1.45 (s, 9H); 1.85–1.95 (m, 2H); 3.8–4.0 (m, 2H); 6.1 (s, 1H); 6.8–7.6 (m, 3H).

(c) Preparation of Ethyl 3-(3',5'-di-tert-Butyl-6-methoxymethoxy-2'-pentyloxy-3-biphenylyl)acrylate:

In a manner similar to that of Example 1(c), by reaction of 3 g (9.5 mmol) of 3,5-di-tert-butyl-2-pentyloxyphenylboronic acid with 2 g (6.35 mmol) of ethyl 3-(3-bromo-4-methoxymethoxyphenyl)acrylate, 2.1 g (65%) of the expected ethyl ester are obtained.

$^1$H NMR (d, CDCl$_3$): 0.7 (t, J=7 Hz, 3H); 1.0 (m, 4H); 1.2 (m, 5H); 1.25 (s, 9H); 1.35 (s, 9H); 3.2–3.3 (m, 2H); 3.35 (s, 3H); 4.2 (q, J=7 Hz, 2H); 5.1 (s, 2H); 6.25 (d, J=16 Hz, 1H); 7.05 (d, J=2.5 Hz, 1H); 7.15 (d, J=8.5 Hz, 1H); 7.3 (d, J=2.5 Hz, 1H); 7.4 (dd, J=8.5 Hz and 2.5 Hz, 1H); 7.5 (d, J=2.5 Hz, 1H); 7.6 (d, J=16 Hz, 1H).

(d) Preparation of Ethyl 3-(3',5'-di-tert-Butyl-6-hydroxy-2'-pentyloxy-3-biphenylyl)acrylate:

In a manner similar to that of Example 2(g), starting with 1.84 g (3.6 mmol) of the above ethyl ester, 1.6 g (88%) of the expected compound was obtained.

$^1$H NMR (d, CDCl$_3$): 0.85 (t, J=7 Hz, 3H); 0.9–1.3 (m, 7H); 1.35 (s, 9H); 1.45 (s, 9H); 1.45–1.6 (m, 2H); 3.5–3.65 (m, 2H); 4.3 (q, J=7 Hz, 2H); 6.35 (d, J=16 Hz, 1H); 7.05 (d, J=8 Hz, 1H); 7.15 (d, J=2.4 Hz, 1H); 7.4 (d, J=2.4 Hz, 1H); 7.5–7.6 (m, 2H); 7.7 (d, J=16 Hz, 1H).

(e) Synthesis of 3-(3',5'-di-tert-Butyl-6-hydroxy-2'-pentyloxy-3-biphenylyl)acrylic Acid:

In a manner similar to that of Example 2(h), starting with 1.62 g (3.2 mmol) of ethyl 3-(3',5'-di-tert-butyl-6-hydroxy-2'-pentyloxy-3-biphenylyl)acrylate, 1.2 g (86%) of 3-(3',5'-di-tert-butyl-6-hydroxy-2'-pentyloxy-3-biphenylyl)acrylic acid having a melting point of 166°–7° C. was obtained.

$^1$H NMR (d, CDCl$_3$): 0.8 (t, J=7 Hz, 3H); 1.1–1.25 (m, 4H); 1.35 (s, 9H); 1.45 (s, 9H); 1.6 (t, J=7 Hz, 2H); 3.5–3.6 (m, 2H); 6.4 (d, J=16 Hz, 1H); 7.1 (d, J=8 Hz, 1H); 7.2 (s, 1H); 7.4 (m, 2H); 7.5–7.6 (m, 2H); 7.8 (d, J=16 Hz, 1H).

Example 4

Synthesis of 3-(3',5'-di-tert-Butyl-6-hydroxy-2'-methoxy-3-biphenylyl)acrylic Acid (a) Preparation of Ethyl 3-(3',5'-di-tert-Butyl-2'-methoxy-6-methoxymethoxy-3-biphenylyl)acrylate:

In a manner similar to that of Example 1(c), by reaction of 2.18 g (8.26 mmol) of 3,5-di-tert-butyl-2-pentyloxyphenylboronic acid with 2 g (6.35 mmol) of ethyl 3-(3-bromo-4-methoxymethoxyphenyl)acrylate, 2 g (70%) of the expected ethyl ester were obtained.

$^1$H NMR (d, CDCl$_3$): 1.2–1.3 (m, 3H); 1.35 (s, 9H); 1.45 (s, 9H); 3.3 (s, 3H); 3.4 (s, 3H); 3.8 (q, J=7 Hz, 2H); 5.15 (s, 2H); 6.35 (d, J=16 Hz, 1H); 7.1 (d, J=2 Hz, 1H); 7.2 (d, J=8 Hz, 1H); 7.35 (d, J=2 Hz, 1H); 7.5 (dd, J=8 Hz and J=2 Hz, 1H); 7.6 (d, J=2 Hz, 1H); 7.7 (d, J=16 Hz, 1H).

(b) Preparation of Ethyl 3-(3',5'-di-tert-Butyl-6-hydroxy-2'-methoxy-3-biphenylyl)acrylate:

In a manner similar to that of Example 2(g), starting with 1.45 g (3.17 mmol) of the above ethyl ester, 1.25 g (96%) of the expected compound was obtained.

$^1$H NMR (d, CDCl$_3$): 1.1–1.2 (m, 4H); 1.35 (s, 9H); 1.45 (s, 9H); 3.5 (s, 3H); 4.25 (q, J=7 Hz, 2H); 6.35 (d, J=16 Hz, 1H); 7.05 (d, J=8 Hz, 1H); 7.15 (d, J=2.3 Hz, 1H); 7.4 (d, J=2.3 Hz, 1H); 7.5–7.6 (m, 2H); 7.7 (d, J=16 Hz, 1H).

(c) Synthesis of 3-(3',5'-di-tert-Butyl-6-hydroxy-2'-methoxy-3-biphenylyl)acrylic Acid:

In a manner similar to that of Example 2(h), starting with 1.23 g (3 mmol) of ethyl 3-(3',5'-di-tert-butyl-6-hydroxy-2'-methoxy-3-biphenylyl)acrylate, 800 mg (69%) of 3-(3',5'-di-tert-butyl-6-hydroxy-2'-methoxy-3-biphenylyl)acrylic acid having a melting point of 166°–7° C. were obtained.

$^1$H NMR (d, CDCl$_3$): 1.35 (s, 9H); 1.45 (s, 9H); 3.5 (s, 3H); 6.4 (d, J=16 Hz, 1H); 7.1 (d, J=8 Hz, 1H); 7.2 (d, J=2.5 Hz, 1H); 7.45 (d, J=2.5 Hz, 1H); 7.5–7.6 (m, 2H); 7.8 (d, J=16 Hz, 1H).

Example 5

Synthesis of 3-[3-(3-Benzyloxy-5,5,8,8-tetramethyl-5,6,7,8-tetrahydro-2-naphthyl)-4-methoxymethoxyphenyl]acrylic Acid (a) Preparation of 3-Benzyloxy-2-bromo-5,5,8,8-tetramethyl-5,6,7,8-tetrahydronaphthalene:

In a manner similar to that of Example 1(a), by reaction of 5 9 (25 mmol) of 3-hydroxy-2-bromo-5,5,8,8-tetramethyl-5,6,7,8-tetrahydronaphthalene with 3.5 ml (29.5 mmol) of benzyl bromide, 6.15 g (66%) of the expected compound were obtained.

$^1$H NMR (CDCl$_3$): 1.20 (s, 6H); 1.24 (s, 6H); 1.64 (s, 4H); 5.12 (s, 2H); 6.82 (s, 1H Ar); 7.21 to 7.50 (m, 6H Ar).

(b) Preparation of 3-Benzyloxy-5,5,8,8-tetramethyl-5,6,7,8-tetrahydro-2-naphthylboronic Acid:

In a manner similar to that of Example 1(b), by reaction of 6.15 g (16.5 mmol) of 3-benzyloxy-2-bromo-5,5,8,8-tetramethyl-5,6,7,8-tetrahydronaphthalene with 5.7 ml (24.7 mmol) of triisopropyl borate, 3.5 g (62%) of the expected boronic acid having a melting point of 125°–6° C. were obtained.

$^1$H NMR (CDCl$_3$): 1.26 (s, 6H); 1.29 (s, 6H); 1.68 (s, 4H); 5.12 (s, 2H); 5.83 (s, 2H); 6.88 (s, 1H Ar); 7.35 to 7.43 (m, 5H Ar); 7.80 (s, 1H Ar).

(c) Preparation of Ethyl 3-[3-(3-Benzyloxy-5,5,8,8-tetramethyl-5,6,7,8-tetrahydro-2-naphthyl)-4-methoxymethoxy-phenyl]acrylate:

In a manner similar to that of Example 1(c), by reaction of 3.4 g (10 mmol) of 3-benzyloxy-5,5,8,8-tetramethyl-5,6,7,8-tetrahydro-2-naphthylboronic acid with 3.17 g (10 mmol) of ethyl 3-(3-bromo-4-methoxymethoxy-phenyl)acrylate, 3 g (56%) of the expected ethyl ester were obtained.

$^1$H NMR (CDCl$_3$): 1.27 (s, 12H); 1.33 (t, J=7.1 Hz, 3H); 1.69 (s, 4H); 3.31 (s, 3H); 4.25 (q, J=7.1 Hz, 2H); 5.01 (s, 2H); 5.06 (s, 2H); 6.32 (d, J=15.9 Hz, 1H); 6.89 (s, 1H Ar); 7.19 (s, 1H Ar); 7.21 to 7.31 (m, 6H Ar), 7.46 (dd, J=8.6 Hz, J=2.3 Hz, 1H Ar); 7.52 (d, J=2.3 Hz, 1H Ar); 7.567 (d, J=15.9 Hz, 1H).

(d) Synthesis of 3-[3-(3-Benzyloxy-5,5,8,8-tetramethyl-5,6,7,8-tetrahydro-2-naphthyl)-4-methoxymethoxy-phenyl] acrylic Acid:

In a manner similar to that of Example 2(h), starting with 1.3 g (2.46 mmol) of the above ethyl ester, 1 g (90%) of 3-[3-(3-benzyloxy-5,5,8,8-tetramethyl-5,6,7,8-tetrahydro-2-naphthyl)-4-methoxymethoxyphenyl]acrylic acid having a melting point of 161°–3° C. was obtained.

$^1$H NMR (CDCl$_3$): 1.27 to 1.28 (m, 12H); 1.69 (s, 4H); 3.32 (s, 3H); 5.01 (s, 2H); 5.07 (s, 2H); 6.33 (d, J=16 Hz, 1H); 6.70 (s, 1H Ar); 7.20 (s, 1H Ar); 7.21 to 7.31 (m, 6H Ar); 7.48 (dd, J=8.6 Hz, J=2.1 Hz, 1H Ar); 7.55 (d, J=2 Hz, 1H Ar); 7.55 (d, J=2 Hz, 1H). $^{13}$C NMR (CDCl$_3$): 1099, 32.11, 33.91, 34.69, 35.33, 56.20, 70.76, 95.02, 111.13, 115.23, 115.36, 125.11, 125.76, 12708, 127.61, 127.68, 128.49, 129.25, 129.76, 129.83, 132.29, 137.37, 137.72, 145.74, 147.05, 153.85, 157.49, 172.54.

Example 6

Synthesis of 3-[3-(3-Benzyloxy-5,5,8,8-tetramethyl-5,6,7,8-tetrahydro-2-naphthyl)-4-hydroxyphenyl] acrylic Acid (a) Preparation of Ethyl 3-[3-(3-Benzyloxy-5,5,8,8-tetramethyl-5,6,7,8-tetrahydro-2-naphthyl)-4-hydroxyphenyl]acrylate:

In a manner similar to that of Example 2(g), starting with 1.8 g (3.4 mmol) of ethyl 3-[3-(3-benzyloxy-5,5,8,8-tetramethyl-5,6,7,8-tetrahydro-2-naphthyl)-4-methoxymethoxyphenyl]acrylate, 1.2 g (72%) of ethyl 3-[3-(3-benzyloxy-5,5,8,8-tetramethyl-5,6,7,8-tetrahydro-2-naphthyl)-4-hydroxyphenyl]acrylate was obtained.

$^1$H NMR (CDCl$_3$): 1.25 to 1.29 (m, 12H); 1.31 (t, J=7.1 Hz, 3H); 1.70 (s, 4H); 4.26 (q, J=7.1 Hz, 2H); 5.07 (s, 2H); 6.33 (d, J=16 Hz, 1H); 6.81 (s, 1H OH); 6.99 (s, 1H Ar); 7.01 (d, J=9.8 Hz, 1H Ar); 7.23 (s, 1H Ar); 7.26 to 7.32 (m, 5H Ar); 7.42 (d, J=2.1 Hz, 1H Ar); 7.49 (dd, J=8.3 Hz, J=2.1 Hz, 1H Ar); 7.69 (d, J=16 Hz, 1H).

(b) Synthesis of 3-[3-(3-Benzyloxy-5,5,8,8-tetramethyl-5,6,7,8-tetrahydro-2-naphthyl)-4-hydroxyphenyl]acrylic Acid:

In a manner similar to that of Example 2(h), starting with 1.2 g (2.47 mmol) of the above ethyl ester, 980 mg (98%) of 3-[3-(3-benzyloxy-5,5,8,8-tetramethyl-5,6,7,8-tetrahydro-2-naphthyl)-4-hydroxyphenyl]acrylic acid having a melting point of 123°–4° C. were obtained.

$^1$H NMR (CDCl$_3$): 1.28 to 1.30 (m, 12H); 1.70 (s, 4H); 5.08 (s, 2H); 6.35 (d, J=15.7 Hz, 1H); 6.38 (s, 1H); 7.00 (s, 1H Ar); 7.04 (d, J=7.5 Hz, 1H Ar); 7.24 (s, 1H Ar); 7.25 to 7.37 (m, 5H Ar); 7.45 (d, J=2 Hz, 1H Ar); 7.52 (dd, J=8.4 Hz, J=2 Hz, 1H Ar); 7.80 (d, J=15.9 Hz, 1H). $^{13}$C NMR (CDCl$_3$): 31.88, 32.02, 34.00, 34.65, 34.99, 35.08, 72.30, 112.66, 114.70, 118.16, 124.49, 127.07, 127.23, 127.64, 128.30, 128.68, 129.22, 130.55, 132.19, 136.06, 139.95, 147.01, 147.08, 152.48, 156.45, 172.75.

Example 7

Synthesis of [4-Methoxymethoxy-3-(3,5,5,8,8-pentamethyl-5,6,7,8-tetrahydro-2-naphthyl)phenyl] propynoic Acid (a) Preparation of 2',2'-dibromo-4-methoxymethoxy-3-(3,5,5,8,8-pentamethyl-5,6,7,8-tetrahydro-2-naphthyl)phenyl] ethylene:

4.95 g (14.71 mmol) of 4-methoxymethoxy-3-(3,5,5,8,8-pentamethyl-5,6,7,8-tetrahydro-2-naphthyl)phenyl] carboxaldehyde and 50 ml of dichloromethane were introduced into a round-bottomed flask. 9.75 g (29.4 mmol) of carbon tetrabromide and 15.45 g (58.84 mmol) of triphenylphosphine were added in succession and the mixture was stirred at room temperature for two hours. The reaction medium was evaporated and the residue obtained was purified by chromatography on a silica column eluted with dichloromethane. 6.75 g (88%) of the expected compound were collected.

(b) Preparation of [4-Methoxymethoxy-3-(3,5,5,8,8-pentamethyl-5,6,7,8-tetrahydro-2-naphthyl)phenyl] acetylene:

7.6 g (12.9 mmol) of 2',2'-dibromo-4-methoxymethoxy-3-(3,5,5,8,8-pentamethyl-5,6,7,8-tetrahydro-2-naphthyl)phenyl]ethylene and 50 ml of THF were introduced under a stream of nitrogen into a three-necked flask. 11 ml (27.1 mmol) of a solution of n-butyllithium (2.5M in hexane) were added dropwise at −78° C. and the mixture was permitted to cool to room temperature. The reaction medium was poured into water and extracted with ethyl ether and the organic phase was decanted, dried over magnesium sulfate and evaporated. The residue obtained was purified by chromatography on a silica column eluted with a mixture of heptane and ethyl acetate (98:2). After evaporation of the solvents, 3.68 g (79%) of the expected acetylenic derivative were collected in the form of a yellow oil.

(c) Preparation of Ethyl [4-methoxymethoxy-3-(3,5,5,8,8-pentamethyl-5,6,7,8-tetrahydro-2-naphthyl)phenyl] propynoate:

3.65 g (10.1 mmol) of the above acetylenic compound and 60 ml of THF were introduced under a stream of nitrogen into a three-necked flask. 4.45 ml (11.1 mmol) of n-butyllithium (2.5M in hexane) were added dropwise at −78° C. and the mixture was stirred for thirty minutes. 1.15 ml (12.1 mmol) of ethyl chloroformate was added at −78° C. and the mixture was permitted to cool to room temperature. The reaction medium was poured into an aqueous ammonium chloride solution and extracted with ethyl ether and the organic phase was decanted, dried over magnesium sulfate and evaporated. The residue obtained was purified by chromatography on a silica column eluted with a mixture of heptane and ethyl acetate (98:2). After evaporation of the solvents, 4.14 g (95%) of ethyl [4-methoxy-methoxy-3-(3,5,5,8,8-pentamethyl-5,6,7,8-tetrahydro-2-naphthyl)phenyl] propynoate were collected in the form of a yellow oil.

(d) Synthesis of [4-Methoxymethoxy-3-(3,5,5,8,8-pentamethyl-5,6,7,8-tetrahydro-2-naphthyl)phenyl] propynoic Acid:

In a manner similar to that of Example 2(h), starting from 439 mg (1 mmol) of ethyl [4-methoxy-methoxy-3-(3,5,5,8,8-pentamethyl-5,6,7,8-tetrahydro-2-naphthyl)phenyl] propynoate, 375 mg (91%) of [4-methoxy-methoxy-3-(3,5,5,8,8-pentamethyl-5,6,7,8-tetrahydro-2-naphthyl)phenyl] propynoic acid having a melting point of 168°–170° C. were obtained.

Example 8

Synthesis of 3-[3-(3-Propyloxy-5,5,8,8-tetramethyl-5,6,7,8-tetrahydro-2-naphthyl)-4-methoxymethoxyphenyl]acrylic Acid (a) Preparation of Ethyl 3-[3-(3-Propyloxy-5,5,8,8-tetramethyl-5,6,7,8-tetrahydro-2-naphthyl)-4-methoxymethoxyphenyl]acrylate:

In a manner similar to that of Example 1(c), by reaction of 3 g (10.4 mmol) of (3-propyloxy-5,5,8,8-tetramethyl-5,6,7,8-tetrahydro-2-naphthyl)boronic acid (preparation described in WO 97/33881) with 3.2 g (10.1 mmol) of ethyl 3-(3-bromo-4-methoxymethoxyphenyl)acrylate (prepared in Example 2(c)), after chromatography on a silica column and elution with a mixture of heptane and ethyl acetate (98:2), 2.1 g (43%) of the expected ethyl ester were obtained.

(b) Preparation of 3-[3-(3-Propyloxy-5,5,8,8-tetramethyl-5,6,7,8-tetrahydro-2-naphthyl)-4-methoxymethoxyphenyl]acrylic Acid:

In a manner similar to that of Example 2(h), starting from 724 mg (1.5 mmol) of ethyl 3-[3-(3-propyloxy-5,5,8,8-tetramethyl-5,6,7,8-tetrahydro-2-naphthyl)-4-methoxymethoxyphenyl]acrylate, 620 mg (91%) of 3-[3-(3-propyloxy-5,5,8,8-tetramethyl-5,6,7,8-tetrahydro-2-naphthyl)-4-methoxymethoxyphenyl]acrylic acid having a melting point of 170°–1° C. were obtained.

Example 9

Synthesis of 3-[3-(3-Pentyloxy-5,5,8,8-tetramethyl-5,6,7,8-tetrahydro-2-naphthyl)-4-methoxymethoxyphenyl]acrylic Acid (a) Preparation of 2-Bromo-3-pentyloxy-5,5,8,8-tetramethyl-5,6,7,8-tetrahydronaphthalene:

In a manner similar to that of Example 1(a), by reaction of 5 g (25 mmol) of 3-bromo-5,5,8,8-tetramethyl-5,6,7,8-tetrahydro-2-naphthol with 3.9 ml (29.5 mmol) of 5-iodopentane, 7 g (79%) of the expected compound were obtained in the form of a colorless oil.

(b) Preparation of (3-Pentyloxy-5,5,8,8-tetramethyl-5,6,7,8-tetrahydro-2-naphthyl)boronic Acid:

In a manner similar to that of Example 1(b), starting from 6.9 g (19.5 mmol) of 2-bromo-3-pentyloxy-5,5,8,8-tetramethyl-5,6,7,8-tetrahydronaphthalene, 4.68 g (75%) of the expected boronic compound were obtained.

(c) Preparation of Ethyl 3-[3-(3-pentyloxy-5,5,8,8-tetramethyl-5,6,7,8-tetrahydro-2-naphthyl)-4-methoxymethoxyphenyl]acrylate:

In a manner similar to that of Example 1(c), by reaction of 4 g (12.6 mmol) of (3-pentyloxy-5,5,8,8-tetramethyl-5,6,7,8-tetrahydro-2-naphthyl)boronic acid with 2.64 g (8.4 mmol) of ethyl 3-[3-(3-bromo-4-methoxymethoxyphenyl)acrylate (prepared in Example 2(c)), after chromatography on a silica column eluted with a mixture of heptane and ethyl acetate (98:2), 3.2 g (75%) of the expected ethyl ester were obtained.

(d) Synthesis of 3-[3-(3-pentyloxy-5,5,8,8-tetramethyl-5,6,7,8-tetrahydro-2-naphthyl)-4-methoxymethoxyphenyl]acrylic Acid:

In a manner similar to that of Example 2(h), starting from 1.7 g (3.26 mmol) of ethyl 3-[3-(3-pentyloxy-5,5,8,8-tetramethyl-5,6,7,8-tetrahydro-2-naphthyl)-4-methoxymethoxyphenyl]acrylate, 1.35 g (86%) of 3-[3-(3-pentyloxy-5,5,8,8-tetramethyl-5,6,7,8-tetrahydro-2-naphthyl)-4-methoxymethoxyphenyl]acrylic acid having a melting point of 178°–80° C. was obtained.

Example 10

Synthesis of 3-(5'-Adamantan-1-yl-4'-methoxy-2'-methyl-3-biphenylyl)acrylic Acid:

(a) Preparation of 4-Bromo-3-methylphenol:

80.0 g (740 mmol) of 3-methylphenol and 400 ml of glacial acetic acid were introduced under a nitrogen atmosphere into a 2 liter three-necked flask. The mixture was cooled to 15° C., 38 ml (742 mmol) of bromine were added dropwise, and the mixture was stirred at 15° C. for three hours. The reaction medium was poured into 1 liter of water and extracted with ethyl ether, the organic phase was decanted, washed with water to neutral pH and dried over magnesium sulfate, and the solvents were evaporated. The residue obtained was triturated in heptane, filtered and dried. 70 g (50%) of a white powder having a melting point of 55–56° C. were collected.

(b) Preparation of 2-(1-Adamantyl)-4-bromo-3-methylphenol:

70.0 g (376 mmol) of 4-bromo-3-methylphenol, 63 g (414 mmol) of 1-adamantanol, 500 ml of heptane and 50 ml of dichloromethane were introduced under a nitrogen atmosphere into a 2,000 ml round-bottomed flask. 20 ml (376 mmol) of 98% sulfuric acid were added dropwise and the mixture was stirred at room temperature for 3 hours. The reaction medium was poured into water, neutralized to a pH of 8–9 with sodium bicarbonate solution, and extracted with ethyl acetate, the organic phase was decanted, washed with water to neutral pH and dried over magnesium sulfate, and the solvents were evaporated. The residue obtained was triturated in heptane, filtered and dried. 59 g (49%) of a pinky white powder having a melting point of 139°–141° C. were collected.

(c) Preparation of 2-(1-Adamantyl)-4-bromo-5-methylanisole:

8 g (24.9 mmol) of 2-(1-adamantyl)-4-bromo-3-methylphenol, 75 ml of DMF and 25 ml of THF were introduced under a stream of nitrogen into a 250 ml three-necked flask. 880 mg (27.4 mmol) of sodium hydride (75% in oil) were added in small portions and the mixture was stirred until the evolution of gas had ceased. Then 1.9 ml (30 mmol) of iodomethane was added and the mixture was stirred at room temperature for two hours. The reaction medium was poured into ice-water and extracted with ethyl ether and the organic phase was decanted, dried over magnesium sulfate and evaporated. The residue obtained was triturated in heptane, filtered and dried. 6.44 g (77%) of pale-beige powder having a melting point of 129°–131° C. were collected.

(d) Preparation of 5-(1-Adamantyl)-4-methoxy-2-methylphenylboronic Acid:

6 g (17.9 mmol) of 2-(1-adamantyl)-4-bromo-5-methylanisole and 40 ml of THF were introduced under a stream of nitrogen into a 250 ml three-necked flask. 7.9 ml (19.7 mmol) of n-butyllithium (2.5M in hexane) were added dropwise at −78° C. and the mixture was stirred for 15 minutes; at this same temperature, 5 ml (21.5 mmol) of triisopropyl borate were added and the mixture was stirred for 30 minutes. 20 ml of hydrochloric acid (1N) were added at −50° C. and the mixture was permitted to warm to room temperature. The reaction medium was extracted with ethyl ether and the organic phase was decanted, dried over magnesium sulfate and evaporated. The solid obtained was triturated in heptane, filtered and dried. 4.75 g (88%) of the expected boronic acid having a melting point of 276°–278°

C. were collected, which was used as is in the remainder of the synthesis to follow.

(e) Synthesis of 3-(5'-Adamantan-1-yl-4'-methoxy-2'-methyl-3-biphenylyl)acrylic Acid:

1.0 g (3.33 mmol) of 5-(1-adamantyl)-4-methoxy-2-methylphenylboronic acid obtained above, 580 mg (2.56 mmol) of 3-bromocinnamic acid and 30 ml of DME were introduced under a stream of nitrogen into a 100 ml three-necked flask. 4.5 ml of an aqueous potassium carbonate solution (2M) was added dropwise and the reaction medium was degassed. Then 150 mg (0.13 mmol) of tetrakistriphenylphosphinepalladium(0) were added and the mixture was heated at reflux for 2 hours. Water and ethyl acetate were added to the reaction medium, which was acidified to a pH of 1 with hydrochloric acid (1N). The organic phase was decanted, washed with water, dried over magnesium sulfate and evaporated. The residue obtained was purified by chromatography on a silica column eluted with a mixture of heptane and ethyl acetate (85:15). After evaporation of the solvents, 750 mg of a thick gel were collected, which were left to crystallize under a stream of nitrogen. The yellow crystals thus obtained were recrystallized from ethanol, filtered and dried to yield 452 mg (44%) of 3-(5'-adamantan-1-yl-4'-methoxy-2'-methyl-3-biphenyl) acrylic acid having a melting point of 194°–6° C.

$^1$H NMR (CDCl$_3$): 1.76 (br, 6H), 2.05 (br, 3H), 2.10 (br, 6H), 2.26 (s, 3H), 3.88 (s, 3H), 6.48 (d, J=15.8 Hz, 1H), 6.78 (s, 1H Ar), 7.07 (s, 1H Ar), 7.35 to 7.51 (m, 4H Ar), 7.84 (d, J=15.8 Hz, 1H Ar).

Example 11

Synthesis of 3-(5'-Adamantan-1-yl-6-hydroxy-4'-methoxy-2'-methyl-3-biphenylyl)acrylic Acid (a) Preparation of Ethyl 3-(3-bromo-4-hydroxyphenyl)acrylate:

In a manner similar to that of Example 2(g), by reaction of 10.1 g (20.3 mmol) of ethyl 3-(3-bromo-4-methoxymethoxyphenyl)acrylate obtained in Example 2(c) with 5.4 ml (102 mmol) of 98% sulfuric acid, 3.9 g of ethyl 3-(3-bromo-4-hydroxyphenyl)acrylate (49%) were obtained in the form of a white powder having a melting point of 112°–3° C.

(b) Preparation of Ethyl 3-(5'-Adamantan-1-yl-6-hydroxy-4'-methoxy-2'-methyl-3-biphenylyl)acrylate:

In a manner similar to that of Example 1(c), by reaction of 3.0 g (10 mmol) of 5-(1-adamantyl)-4-methoxy-2-methylphenylboronic acid obtained in Example 10(d) with 2.25 g (8.33 mmol) of ethyl 3-(3-bromo-4-hydroxyphenyl)acrylate obtained above, 570 mg (15%) of a white powder having a melting point of 164°–6° C. were obtained.

(c) Synthesis of 3-(5'-Adamantan-1-yl-6-hydroxy-4'-methoxy-2'-methyl-3-biphenylyl)acrylic Acid:

In a manner similar to that of Example 2(h), starting from 270 mg (0.6 mmol) of ethyl 3-(5'-adamantan-1-yl-6-hydroxy-4'-methoxy-2'-methyl-3-biphenylyl)acrylate obtained above, 190 mg (76%) of a white powder which decomposed commencing at 120° C. were obtained.

$^1$H NMR (CDCl$_3$): 1.76 (br, 6H), 2.07 (br, 9H), 2.13 (s, 3H), 3.89 (s, 3H), 5.20 (br, 1H), 6.31 (d, J=15.75 Hz, 1H), 6.83 (s, 1H), 7.00 (d, J=9.25 Hz, 1H), 7.48 (dd, J=9.25 Hz, J2=2.0 Hz, 1H), 7.74 (d, J=15.75 Hz, 1H).

Example 12

Synthesis of 3-(5'-Adamantan-1-yl-4'-methoxy-6-methoxymethoxy-2'-methyl-3-biphenylyl)acrylic Acid (a) Preparation of Ethyl 3-(5'-adamantan-1-yl-4'-methoxy-6-methoxymethoxy-2'-methyl-3-biphenylyl)acrylate:

In a manner similar to that of Example 2(b), by reaction of 300 mg (0.67 mmol) of ethyl 3-(5'-adamantan-1-yl-6-hydroxy-4'-methoxy-2'-methyl-3-biphenylyl)acrylate obtained in Example 11(b) with 64 mg (0.8 mmol) of methoxymethyl chloride, 320 mg (97%) of a white gel were obtained.

$^1$H NMR (CDCl$_3$): 1.32 (t, J=7.00 Hz, 3H), 1.75 (br, 6H), 2.04+2.09 (br+br, 6H+3H), 2.14 (s, 3H), 3.37 (s, 3H), 3.87 (s, 3H), 4.25 (q, J=7.0 Hz, 2H), 5.11 (s, 2H), 6.33 (d, J=15.8 Hz, 1H), 6.76 (s, 1H), 7.00 (s, 1H), 7.20 (d, J=8.5 Hz, 1H), 7.36 (d, J=2.25 Hz, 1H), 7.46 (dd, J1=8.5 Hz, J2=2.25 Hz, 1H), 7.66 (d, J=15.8 Hz, 1H).

(b) Synthesis of 3-(5'-adamantan-1-yl-4'-methoxy-6-methoxymethoxy-2'-methyl-3-biphenylyl)acrylic Acid In a manner similar to that of Example 2(h), starting from 300 mg (0.61 mmol) of ethyl 3-(5'-adamantan-1-yl-4'-methoxy-6-methoxymethoxy-2'-methyl-3-biphenylyl) acrylate obtained above, 200 mg (71%) of a white powder decomposed commencing at 113° C. were obtained.

$^1$H NMR (CDCl$_3$): 1.76 (br, 6H), 2.04 (br, 3H), 2.09 (br, 6H), 2.14 (s, 3H), 3.38 (s, 3H), 3.87 (s, 3H), 5.13 (s, 2H), 6.34 (d, J=15.75 Hz, 1H), 6.76 (s, 1H), 7.00 (s, 1H), 7.22 (d, J=8.5 Hz, 1H), 7.39 (d, J=2.25 Hz, 1H), 7.49 (dd, J1=8.5 Hz, J2=2.25 Hz, 1H), 7.76 (d, J=15.75 Hz, 1H).

Example 13

Synthesis of 3-{4-Methoxy-3-[3-(3-methoxybenzyloxy)-5,5,8,8-tetramethyl-5,6,7,8-tetrahydro-2-naphthyl]phenyl}acrylic Acid (a) Preparation of 2-Bromo-3-methoxymethoxy-5,5,8,8-tetramethyl-5,6,7,8-tetrahydronaphthalene:

In a manner similar to that of Example 1(a), by reaction of 100 g (353 mmol) of 3-bromo-5,5,8,8-tetramethyl-5,6,7,8-tetrahydro-2-naphthol with 32 ml (406 mmol) of methoxymethyl chloride, 100 g (86%) of the expected compound were obtained in the form of a beige powder having a melting point of 69°–71° C.

(b) Preparation of 3-Methoxymethoxy-5,5,8,8-tetramethyl-5,6,7,8-tetrahydro-2-naphthylboronic Acid:

In a manner similar to that of Example 1(b), by reaction of 90 g (275 mmol) of 2-bromo-3-methoxy-methoxy-5,5,8,8-tetramethyl-5,6,7,8-tetrahydro-naphthalene obtained above, 70 g (87%) of the expected compound were obtained in the form of a white powder having a melting point of 130°–132° C.

(c) Preparation of 3-Bromo-4-methoxybenzaldehyde:

In a manner similar to that of Example 1(a), by reaction of 50 g (270 mmol) of 3-bromo-4-hydroxybenzaldehyde (obtained in accordance with Example 2(a)) and 20.2 ml (338 mmol) of iodomethane, 48 g (83%) of the expected compound were obtained in the form of a white powder having a melting point of 48°–50° C.

(d) Preparation of Ethyl 3-(3-bromo-4-methoxyphenyl)acrylate:

In a manner similar to that of Example 2(c), by reaction of 46 g (214 mmol) of 3-bromo-4-methoxybenzaldehyde obtained above and 55.2 ml (278 mmol) of triethyl phosphonoacetate, 47 g (77%) of the expected compound were obtained in the form of white flakes having a melting point of 76°–78° C.

(e) Preparation of Ethyl 3-[4-Methoxy-3-(3-methoxymethoxy-5,5,8,8-tetramethyl-5,6,7,8-tetrahydro-2-naphthyl)phenyl]acrylate:

In a manner similar to that of Example 1(c), by reaction of 53.3 g (182 mmol) of 3-methoxymethoxy-5,5,8,8-tetramethyl-5,6,7,8-tetrahydro-2-naphthylboronic acid obtained in Example 13(b) and 40 g (140 mmol) of ethyl 3-(3-bromo-4-methoxyphenyl)acrylate obtained above, 63 g (99%) of the expected compound were obtained in the form of a thick yellow oil.

$^1$H NMR (CDCl$_3$): 1.23 to 1.35 (m, 15H), 1.70 (s, 4H), 3.34 (s, 3H), 3.81 (s, 3H), 4.25 (q, J=7.25 Hz, 2H), 5.03 (s, 2H), 6.32 (d, J=15.75 Hz, 1H), 9.95 (d, J=9.0 Hz, 1H), 7.13 (s, 1H), 7.42 to 7.66 (m, 2H), 7.67 (d, J=15.75 Hz, 1H).

(f) Preparation of Ethyl 3-[3-(3-Hydroxy-5,5,8,8-tetramethyl, 5,6,7,8-tetrahydro-2-naphthyl)-4-methoxyphenyl]acrylate:

In a manner similar to that of Example 2(g), by reaction of 63 g (140 mmol) of ethyl 3-[4-methoxy-3-(3-methoxymethoxy-5,5,8,8-tetramethyl-5,6,7,8-tetrahydro-2-naphthyl)phenyl]acrylate obtained above and 22 ml (420 mmol) of sulfuric acid, 42.5 g (75%) of the expected compound were obtained in the form of a pale-yellow powder with a melting point of 147–149° C.

(g) Preparation of Ethyl 3-{4-Methoxy-3-[3-(3-methoxybenzyloxy)-5,5,8,8-tetramethyl-5,6,7,8-tetrahydro-2-naphthyl]phenyl}acrylate:

In a manner similar to that of Example 1(a), by reaction of 1 g (2.45 mmol) of ethyl 3-[3-(3-hydroxy-5,5,8,8-tetramethyl-5,6,7,8-tetrahydro-2-naphthyl)-4-methoxyphenyl]acrylate obtained above with 4 ml (3 mmol) of 3-methoxybenzyl chloride, 1.30 g (100%) of the expected compound was obtained in the form of a yellow oil.

$^1$H NMR (CDCl$_3$): 1.24 to 1.35 (m, 15H), 1.69 (s, 4H), 3.69 (s, 3H), 3.76 (s, 3H), 4.25 (q, J=7.0 Hz, 2H), 5.0 (s, 2H), 6.30 (d, J=16.0 Hz, 1H), 6.75 to 6.96 (m, 5H), 7.16 to 7.22 (m, 2H), 7.45 to 7.51 (m, 2H), 7.67 (d, J=16.0 Hz, 1H).

(h) Synthesis of 3-{4-Methoxy-3-[3-(3-methoxybenzyloxy)-5,5,8,8-tetramethyl-5,6,7,8-tetrahydro-2-naphthyl]phenyl}acrylic Acid:

In a manner similar to that of Example 2(h), starting from 1.3 g (2.45 mmol) of ethyl 3-{4-methoxy-3-[3-(3-methoxybenzyloxy)-5,5,8,8-tetramethyl-5,6,7,8-tetrahydro-2-naphthyl]phenyl}acrylate obtained above, 830 mg (67%) of the expected compound were obtained in the form of a white powder having a melting point of 168°–170° C.

Example 14

Synthesis of 3-{4-Methoxy-3-[3-(4-methoxybenzyloxy)-5,5,8,8-tetramethyl-5,6,7,8-tetrahydro-2-naphthyl]phenyl}acrylic Acid (a) Preparation of Ethyl 3-{4-Methoxy-3-[3-(4-methoxybenzyloxy)-5,5,8,8-tetramethyl-5,6,7,8-tetrahydro-2-naphthyl]phenyl}acrylate:

In a manner similar to that of Example 1(a), by reaction of 1.23 g (3 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 490 μl (3.6 mmol) of 4-methoxybenzyl chloride, 1.58 g (100%) of the expected product are obtained in the form of a yellow oil.

$^1$H NMR (CDCl$_3$): 1.21 to 1.35 (m, 15H), 1.69 (s, 4H), 3.75 (s, 3H), 3.77 (s, 3H), 4.25 (q, J=7.0 Hz, 2H), 4.93 (s, 2H), 6.29 (d, J=16.0 Hz, 1H), 6.80 to 6.94 (m, 4H), 7.15 to 7.18 (m, 2H), 7.31 (d, J=8.5 Hz, 1H), 7.44 to 7.50 (m, 2H), 7.66 (d, J=16.25 Hz, 1H).

(b) Synthesis of 3-{4-Methoxy-3-[3-(4-methoxybenzyloxy)-5,5,8,8-tetramethyl-5,6,7,8-tetrahydro-2-naphthyl]phenyl}acrylic Acid:

In a manner similar to that of Example 2(h), starting from 1.58 g (3 mmol) of ethyl 3-{4-methoxy-3-[3-(4-methoxybenzyloxy)-5,5,8,8-tetramethyl-5,6,7,8-tetrahydro-2-naphthyl]phenyl}acrylate obtained above, 1.1 g (71%) of the expected compound was obtained in the form of a white powder having a melting point of 201°–203° C.

Example 15

Synthesis of 3-{3-[3-(6-Hydroxyhexyloxy)-5,5,8,8-tetramethyl-5,6,7,8-tetrahydro-2-naphthyl]-4-methoxyphenyl}acrylic Acid (a) Preparation of Ethyl 3-{3-[3-(6-Hydroxyhexyloxy)-5,5,8,8-tetramethyl-5,6,7,8-tetrahydro-2-naphthyl]-4-methoxyphenyl}acrylate:

In a manner similar to that of Example 1(a), by reaction of 1.4 g (3.4 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 540 μl (4.1 mmol) of 1-bromohexanol, 850 mg (50%) of the expected compound were obtained in the form of a yellow oil.

$^1$H NMR (CDCl$_3$): 1.23 to 1.35 (m, 19H), 1.43 to 1.70 (m, 8H), 3.56 (q, J=5.5 Hz, 2H), 3.81 (s, 3H), 3.90 (t, J=5.0 Hz, 2H), 4.25 (q, J=7.25 Hz, 2H), 6.31 (d, J=16.0 Hz, 1H), 6.85 (s, 1H), 6.96 (d, J=8.5 Hz, 1H), 7.20 (s, 1H), 7.47 (dd, J1=8.25 Hz, J2=2.25 Hz, 1H), 7.52 (d, J=2.25 Hz, 1H), 7.67 (d, J=16.0 Hz, 1H).

(b) Synthesis of 3-{3-[3-(6-Hydroxyhexyloxy)-5,5,8,8-tetramethyl-5,6,7,8-tetrahydro-2-naphthyl]-4-methoxyphenyl}acrylic Acid:

In a manner similar to that of Example 2(h), starting from 850 mg (1.67 mmol) of ethyl 3-{3-[3-(6-Hydroxyhexyloxy)-5,5,8,8-tetramethyl-5,6,7,8-tetrahydro-2-naphthyl]-4-methoxyphenyl}acrylate obtained above, 510 mg (63%) of the expected compound were obtained in the form of a white powder having a melting point of 118°–120° C.

Example 16

Synthesis of 3-{3-[3-(7-Hydroxyheptyloxy)-5,5,8,8-tetramethyl-5,6,7,8-tetrahydro-2-naphthyl]-4-methoxyphenyl}acrylic Acid (a) Preparation of Ethyl 3-{3-[3-(7-Hydroxyheptyloxy)-5,5,8,8-tetramethyl-5,6,7,8-tetrahydro-2-naphthyl]-4-methoxyphenyl}acrylate:

1.23 g (3 mmol) of ethyl 3-[3-(3-hydroxy-5,5,8,8-tetramethyl-5,6,7,8-tetrahydro-2-naphthyl]-4-methoxyphenyl]acrylate obtained in Example 13(f), 440 mg (3.2 mmol) of potassium carbonate, 540 μl (3.5 mmol) of 1-bromoheptanol and 30 ml of butanone were introduced into a round-bottomed flask. The mixture was heated at reflux for 8 hours, the reaction medium was poured into water, acidified to a pH of 1 with hydrochloric acid and extracted with ethyl ether, and the organic phase was decanted, dried over magnesium sulfate and evaporated. 1.57 g (100%) of the expected compound in the form of a yellow oil was collected.

$^1$H NMR (CDCl$_3$): 1.26 (s, 6H), 1.32 (s, 6H), 1.08 to 1.7 (m, 17H), 3.5 to 3.7 (m, 2H), 3.81 (s, 3H), 3.89 (t, J=6.25 Hz, 2H), 4.24 (q, J=7.0 Hz, 2H), 6.3 (d, J=16.0 Hz, 1H), 6.84 (s, 1H), 6.95 (d, J=8.25 Hz, 1H), 7.19 (s, 1H), 7.47 (dd, J1=8.25 Hz, J2=2.25 Hz, 1H), 7.50 (d, J=2.25 Hz, 1H), 7.67 (d, J=16.0 Hz, 1H).

(b) Synthesis of 3-{3-[3-(7-Hydroxyheptyloxy)-5,5,8,8-tetramethyl-5,6,7,8-tetrahydro-2-naphthyl]-4-methoxyphenyl}acrylic Acid:

In a manner similar to that of Example 2(h), starting from 1.57 g (3 mmol) of ethyl 3-{3-[3-(7-hydroxyheptyloxy)-5,5,8,8-tetramethyl-5,6,7,8-tetrahydro-2-naphthyl]-4-methoxyphenyl}acrylate obtained above, 700 mg (47%) of the expected compound were obtained in the form of a white powder having a melting point of 105°–107° C.

Example 17

Synthesis of 3-{3-[3-(5-Hydroxypentyloxy)-5,5,8,8-tetramethyl-5,6,7,8-tetrahydro-2-naphthyl]-4-methoxyphenyl}acrylic Acid (a) Preparation of Ethyl 3-{3-[3-(5-Acetoxypentyloxy)-5,5,8,8-tetramethyl-5,6,7,8-tetrahydro-2-naphthyl]-4-methoxyphenyl}acrylate:

In a manner similar to that of Example 1(a), by reaction of 1.20 g (2.90 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 727 mg (3.48 mmol) of 5-bromopentyl acetate, 1.42 g (92%) of the expected compound was obtained in the form of a yellow oil.

$^1$H NMR (CDCl$_3$): 1.26 to 1.37 (m, 17H), 1.50 to 1.67 (m, 4H), 1.70 (s, 4H), 2.01 (s, 3H), 3.80 (s, 3H), 3.80 to 4.00 (m, 4H), 4.25 (q, J=7.25 Hz, 2H), 6.30 (d, J=15.75 Hz, 1H), 6.84 (s, 1H), 6.94 (d, J=8.25 Hz, 1H), 7.17 (s, 1H), 7.44 to 7.48 (m, 2H), 7.66 (d, J=16.0 Hz, 1H).

(b) Synthesis of 3-{3-[3-(5-Hydroxypentyloxy)-5,5,8,8-tetramethyl-5,6,7,8-tetrahydro-2-naphthyl]-4-methoxyphenyl}acrylic Acid:

In a manner similar to that of Example 2(h), starting from 1.42 g (2.65 mmol) of ethyl 3-{3-[3-(5-acetoxypentyloxy)-5,5,8,8-tetramethyl-5,6,7,8-tetrahydro-2-naphthyl]-4-methoxyphenyl}acrylate obtained above, 730 mg (60%) of the expected compound were obtained in the form of a white powder having a melting point of 115°–117° C.

Example 18

Synthesis of 3-{3-[3-(3-Hydroxypropyloxy)-5,5,8,8-tetramethyl-5,6,7,8-tetrahydro-2-naphthyl]-4-methoxyphenyl}acrylic Acid (a) Preparation of Ethyl 3-{3-[3-(3-Hydroxypropyloxy)-5,5,8,8-tetramethyl-5,6,7,8-tetrahydro-2-naphthyl]-4-methoxyphenyl}acrylate:

In a manner similar to that of Example 16(a), by reaction of 1.2 g (2.9 mmol) of ethyl 3-[3-(3-hydroxy-5,5,8,8-tetramethyl-5,6,7,8-tetrahydro-2-naphthyl]-4-methoxyphenyl]acrylate obtained in Example 13(f) with 490 mg (3.5 mmol) of 1-bromopropanol, 632 mg (47%) of the expected compound were obtained in the form of a yellow oil.

$^1$H NMR (CDCl$_3$): 1.27 to 1.35 (m, 9H), 1.70 (s, 4H), 1.85 to 1.92 (m, 2H), 1.96 (br, 1H), 3.64 (m, 2H), 3.82 (s, 3H), 4.09 (t, J=5.5 Hz, 2H), 4.25 (q, J=7.25 Hz, 2H), 6.31 (d, J=16.0 Hz, 1H), 6.87 (s, 1H), 6.96 (d, J=8.5 Hz, 1H), 7.15 (s, 1H), 7.44 (d, J=2.25 Hz, 1H), 7.49 (dd, J1=8.5 Hz, J2=2.25 Hz, 1H), 7.66 (d, J=16.0 Hz, 1H).

(b) Synthesis of 3-{3-[3-(3-Hydroxypropyloxy)-5,5,8,8-tetramethyl-5,6,7,8-tetrahydro-2-naphthyl]-4-methoxyphenyl}acrylic Acid:

In a manner similar to that of Example 2(h), starting from 632 mg (1.35 mmol) of ethyl 3-{3-[3-(3-hydroxypropyloxy)-5,5,8,8-tetramethyl-5,6,7,8-tetrahydro-2-naphthyl]-4-methoxyphenyl}acrylate obtained above, 449 mg (75%) of the expected compound obtained in the form of a white powder having a melting point of 198°–200° C.

Example 19

Synthesis of the Intermediate 3-[3-(1-methoxymethoxy-5,5,8,8-tetramethyl-5,6,7,8-tetrahydro-2-naphthyl)phenyl]acrylic Acid (a) Preparation of 1-Methoxymethoxy-5,5,8,8-tetramethyl-5,6,7,8-tetrahydronaphthalene:

In a manner similar to that of Example 1(a), by reaction of 8.65 g (42.4 mmol) of 5,5,8,8-tetramethyl-5,6,7,8-tetrahydro-2-naphthol with 3.55 ml (46.6 mmol) of methoxymethyl chloride, 10.5 g (100%) of the expected compound were obtained.

(b) Preparation of 1-Methoxymethoxy-5,5,8,8-tetramethyl-5,6,7,8-tetrahydro-2-naphthaleneboronic Acid:

1 g (4 mmol) of 1-methoxymethoxy-5,5,8,8-tetramethyl-5,6,7,8-tetrahydronaphthalene and 12 ml of THF were introduced into a round-bottomed flask. The mixture was cooled to −78° C. and 630 μl (4.2 mmol) of TMEDA and then 3.4 ml (4.4 mmol) of sec-BuLi (1.3M) were added dropwise. The mixture was stirred at −78° C. for 1 hour and then 1.4 ml (6 mmol) of triisopropyl borate was added and the mixture was permitted to warm to room temperature. 3 ml of hydrochloric acid (5%) were added at −40° C. and the mixture was stirred at room temperature for 1 hour. The reaction medium was poured into water and extracted with ethyl acetate and the organic phase was decanted, dried over magnesium sulfate and evaporated. The residue obtained is purified by chromatography on a silica column eluted with a mixture of dichloromethane and methanol (98:2). 900 mg (77%) of the expected boronic compound in the form of a pale-yellow oil were collected.

(c) Synthesis of 3-[3-(1-Methoxymethoxy-5,5,8,8-tetramethyl-5,6,7,8-tetrahydro-2-naphthyl)phenyl]acrylic Acid:

In a manner similar to that of Example 1(c), by reaction of 3.4 g (11.6 mmol) of 1-methoxymethoxy-5,5,8,8-tetramethyl-5,6,7,8-tetrahydro-2-naphthalene-boronic acid with 1.32 g (5.8 mmol) of 3-bromocinnamic acid, trituration in heptane gave 1.4 g (62%) of 3-[3-(1-methoxymethoxy-5,5,8,8-tetramethyl-5,6,7,8-tetrahydro-2-naphthyl)phenyl]acrylic acid in the form of a white powder having a melting point of 188°–9° C.

Example 20

Synthesis of 3-[3-(1-Benzyloxy-5,5,8,8-tetramethyl-5,6,7,8-tetrahydro-2-naphthyl)phenyl]acrylic Acid (a) Preparation of Methyl 3-[3-(1-Hydroxy-5,5,8,8-tetramethyl-5,6,7,8-tetrahydro-2-naphthyl)phenyl]acrylate:

1.24 g (3.15 mmol) of 3-[3-(1-methoxymethoxy-5,5,8,8-tetramethyl-5,6,7,8-tetrahydro-2-naphthyl)phenyl]acrylic acid obtained in Example 19(c), 15 ml of methanol and 15 ml of THF were introduced into a round-bottomed flask. 620 μl of concentrated sulfuric acid were added and the mixture was stirred at room temperature for eight hours and heated at reflux for two hours. The reaction medium was poured into water and extracted with ethyl ether and the organic phase was decanted, dried over magnesium sulfate and evaporated. 1.1 g (100%) of methyl 3-[3-(1-hydroxy-5,5,8,8-tetramethyl-5,6,7,8-tetrahydro-2-naphthyl)phenyl]acrylate having a melting point of 197°–8° C. were collected.

(b) Preparation of Methyl 3-[3-(1-Benzyloxy-5,5,8,8-tetramethyl-5,6,7,8-tetrahydro-2-naphthyl)phenyl]acrylate:

In a manner similar to that of Example 1(a), by reaction of 500 mg (1.37 mmol) of methyl 3-[3-(1-hydroxy-5,5,8,8- tetramethyl-5,6,7,8-tetrahydro-2-naphthyl)phenyl]acrylate with 180 µl (1.5 mmol) of benzyl bromide, 550 mg (88%) of the expected compound were obtained in the form of a yellow oil.

(c) Synthesis of 3-[3-(1-Benzyloxy-5,5,8,8-tetramethyl-5,6,7,8-tetrahydro-2-naphthyl)phenyl]acrylic Acid:

In a manner similar to that of Example 2(h), starting from 498 mg (1.01 mmol) of ethyl 3-[3-(1-benzyloxy-5,5,8,8-tetramethyl-5,6,7,8-tetrahydro-2-naphthyl)phenyl]acrylate, 360 mg (82%) of 3-[3-(1-benzyloxy-5,5,8,8-tetramethyl-5,6,7,8-tetrahydro-2-naphthyl)phenyl]acrylic acid having a melting point of 153°–4° C. were obtained.

Example 21

Synthesis of 3-{3-[3-(5-tert-Butoxycarbonylpentyloxy)-5,5,8,8-tetramethyl-5,6,7,8-tetrahydro-2-naphthyl]-4-methoxyphenyl}acrylic Acid (a) Preparation of tert-Butyl 6-bromohexanoate:

1.95 g (10 mmol) of 6-bromohexanoic acid dissolved in 10 ml of dichloromethane were introduced under a stream of nitrogen into a round-bottomed flask. A solution of 4.37 g (20 mmol) of tert-butyl 2,2,2-trichloroacetimidate in 20 ml of cyclohexane was added dropwise, followed immediately by 200 µl of trifluoroborane etherate. The mixture was stirred at room temperature for 5 minutes, 5 g of sodium bicarbonate were added, and the mixture was stirred for 1 minute. The suspension obtained was placed on a silica column which had been wetted beforehand with cyclohexane and the latter was eluted with a 8:2 cyclohexane/ethyl acetate mixture. After evaporation of the solvents, 1.63 g (65%) of a colorless oil was obtained.

$^1$H NMR (CDCl$_3$): 1.45 (s, 9H), 1.44 to 1.70 (m, 4H), 1.87 (m, 2H), 2.23 (t, J=7.5 Hz, 2H), 3.41 (t, J=6.75 Hz, 2H).

(b) Preparation of Ethyl 3-{3-[3-(5-tert-Butoxycarbonylpentyloxy)-5,5,8,8-tetramethyl-5,6,7,8-tetrahydro-2-naphthyl]-4-methoxyphenyl}acrylate:

In a manner similar to that of Example 1(a), by reaction of 2.36 g (5.8 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 1.6 g (6.3 mmol) of tert-butyl 6-bromohexanoate obtained above, 3.3 g (100%) of the expected compound were obtained in the form of a yellow oil.

$^1$H NMR (CDCl$_3$): 1.21 to 1.75 (m, 32H), 2.13 (t, J=7.25 Hz, 2H), 3.80 (s, 3H), 3.88 (t, J=6.25 Hz, 2H), 4.25 (q, J=7.0 Hz, 2H), 6.30 (d, J=16.0 Hz, 1H), 6.83 (s, 1H), 6.94 (d, J=8.75 Hz, 1H), 7.16 (s, 1H), 7.44 to 7.48 (m, 2H), 7.66 (d, J=16.0 Hz, 1H).

(c) Synthesis of 3-{3-[3-(5-tert-Butoxycarbonylpentyloxy)-5,5,8,8-tetramethyl-5,6,7,8-tetrahydro-2-naphthyl]-4-methoxyphenyl}acrylic Acid:

A solution of 1.0 g (1.7 mmol) of ethyl 3-{3-[3-(5-tert-butoxycarbonylpentyloxy)-5,5,8,8-tetramethyl-5,6,7,8-tetrahydro-2-naphthyl]-4-methoxyphenyl}acrylate obtained above dissolved in 25 ml of THF was placed in a round-bottomed flask and 730 mg (17 mmol) of lithium hydroxide and 2 ml of water were added. The mixture was heated at the reflux of the THF for 8 hours and stirred at room temperature for 48 hours, the reaction medium was poured into water, acidified to a pH of 1 with hydrochloric acid and extracted with ethyl ether, and the organic phase was decanted, dried over magnesium sulfate, filtered and evaporated. The residue obtained was chromatographed on a silica column eluted with a 8:2 heptane/ethyl acetate mixture. After evaporation of the solvents, 126 mg (14%) of a white powder having a melting point of 130°–132° C. were collected.

Example 22

Synthesis of 3-{3-[3-(7-tert-Butoxycarbonylheptyloxy)-5,5,8,8-tetramethyl-5,6,7,8-tetrahydro-2-naphthyl]-4-methoxyphenyl}acrylic Acid (a) Preparation of tert-butyl 8-Bromooctanoate:

In a manner similar to that of Example 21(a), starting from 3 g (13.4 mmol) of 8-bromooctanoic acid, 3 g (80%) of a pale-yellow oil were obtained.

$^1$H NMR (CDCl$_3$): 1.29 to 1.37 (m, 6H), 1.44 (s, 9H), 1.50 to 1.75 (m, 2H), 1.75 to 1.95 (m, 2H), 2.20 (t, J=7.5 Hz, 2H), 3.40 (t, J=6.75 Hz, 2H).

(b) Preparation of Ethyl 3-{3-[3-(7-tert-Butoxycarbonylheptyloxy)-5,5,8,8-tetramethyl-5,6,7,8-tetrahydro-2-naphthyl]-4-methoxyphenyl}acrylate:

In a manner similar to that of Example 1(a), by reaction of 3.82 g (9.34 mmol) of ethyl 3-[3-(3-hydroxy-5,5,8,8-tetramethyl-5,6,7,8-tetrahydro-2-naphthyl]-4-methoxyphenyl}acrylate obtained in Example 13(f) with 3 g (10.7 mmol) of tert-butyl 8-bromooctanoate obtained above, 4.36 g (77%) of the expected compound were obtained in the form of a yellow oil.

$^1$H NMR (CDCl$_3$): 1.26 to 1.13 (m, 21H), 1.44 (s, 9H), 1.43 to 1.65 (m, 4H), 1.70 (s, 4H), 2.16 (t, J=7.25 Hz, 2H), 3.80 (s, 3H), 3.88 (t, J=6.5 Hz, 2H), 4.24 (q, J=7.0 Hz, 2H), 6.30 (d, J=15.75 Hz, 1H), 6.84 (s, 1H), 6.93 (d, J=8.25 Hz, 1H), 7.17 (s, 1H), 7.43 to 7.49 (m, 2H), 7.66 (d, J=15.75 Hz, 1H).

(c) Synthesis of 3-{3-[3-(7-tert-Butoxycarbonylheptyloxy)-5,5,8,8-tetramethyl-5,6,7,8-tetrahydro-2-naphthyl]-4-methoxyphenyl}acrylic Acid:

In a manner similar to that of Example 21(c), starting from 1.15 g (1.9 mmol) of ethyl 3-{3-[3-(7-tert-butoxycarbonylheptyloxy)-5,5,8,8-tetramethyl-5,6,7,8-tetrahydro-2-naphthyl]-4-methoxyphenyl}acrylate obtained above, 363 mg (33%) of the expected compound were obtained in the form of a white powder having a melting point of 126°–128° C.

Example 23

Synthesis of 3-{3-[3-(7-Carboxyheptyloxy)-5,5,8,8-tetramethyl-5,6,7,8-tetrahydro-2-naphthyl]-4-methoxyphenyl}acrylic Acid (a) Preparation of Ethyl 3-{3-[3-(7-Carboxyheptyloxy)-5,5,8,8-tetramethyl-5,6,7,8-tetrahydro-2-naphthyl]-4-methoxyphenyl}acrylate:

A solution of 3.75 g (6.18 mmol) of ethyl 3-{3-[3-(7-tert-butoxycarbonylheptyloxy)-5,5,8,8-tetramethyl-5,6,7,8-tetrahydro-2-naphthyl]-4-methoxyphenyl}acrylate obtained in Example 22(b) dissolved in 60 ml of dichloromethane was placed in a round-bottomed flask, 4.76 ml (61.8 mmol) of trifluoroacetic acid were added, and the mixture was stirred at room temperature for 4 hours. The reaction medium was poured into water and extracted with ethyl ether, and the organic phase was decanted, dried over magnesium sulfate, filtered and evaporated. 3.4 g (100%) of the expected compound were obtained in the form of a white foam.

$^1$H NMR (CDCl$_3$): 1.26 to 1.35 (m, 21H), 1.50 to 1.67 (m, 4H), 1.70 (s, 4H), 2.30 (t, J=7.5 Hz, 2H), 3.80 (s, 3H), 3.88 (t, J=6.25 Hz, 2H), 4.25 (q, J=7.25 Hz, 2H), 6.31 (d, J=15.75 Hz, 1H), 6.84 (s, 1H), 6.94 (d, J=8.25 Hz, 1H), 7.17 (s, 1H), 7.44 to 7.49 (m, 2H), 7.67 (d, J=16.0 Hz, 1H).

(b) Synthesis of 3-{3-[3-(7-Carboxyheptyloxy)-5,5,8,8-tetramethyl-5,6,7,8-tetrahydro-2-naphthyl]-4-methoxyphenyl}acrylic Acid:

In a manner similar to that of Example 2(h), starting from 1 g (1.8 mmol) of ethyl 3-{3-[3-(7-carboxyheptyloxy)-5,5,8,8-tetramethyl-5,6,7,8-tetrahydro-2-naphthyl]-4-methoxyphenyl}acrylate obtained above, 830 mg (88%) of the expected compound were obtained in the form of a white powder having a melting point of 212°–214° C.

Example 24

Synthesis of 3-{3-[3-(5-Carboxypentyloxy)-5,5,8,8-tetramethyl-5,6,7,8-tetrahydro-2-naphthyl]-4-methoxyphenyl}acrylic Acid (a) Preparation of Ethyl 3-{3-[3-(5-Carboxypentyloxy)-5,5,8,8-tetramethyl-5,6,7,8-tetrahydro-2-naphthyl]-4-methoxyphenyl}acrylate:

In a manner similar to that of Example 23(a), starting from 2.3 g (3.97 mmol) of ethyl 3-{3-[3-(5-tert-butoxycarbonylpentyloxy)-5,5,8,8-tetramethyl-5,6,7,8-tetrahydro-2-naphthyl]-4-methoxyphenyl}acrylate obtained in Example 21(b), 2.1 g (100%) of the expected compound were obtained in the form of a white foam.

$^1$H NMR (CDCl$_3$): 1.24 to 1.42 (m, 17H), 1.55 to 1.70 (m, 8H), 2.28 (t, J=7.0 Hz, 2H), 3.80 (s, 3H), 3.91 (t, J=5.75 HZ, 2H), 4.25 (q, J=7.25 Hz, 2H), 6.32 (d, J=15.75 Hz, 1H), 6.84 (s, 1H), 6.95 (d, J=9.0 Hz, 1H), 7.19 (s, 1H), 7.46 to 7.50 (m, 2H), 7.69 (d, J=16.0 Hz, 1H).

(b) Synthesis of 3-{3-[3-(5-Carboxypentyloxy)-5,5,8,8-tetramethyl-5,6,7,8-tetrahydro-2-naphthyl]-4-methoxyphenyl}acrylic Acid:

In a manner similar to that of Example 2(h), starting from 900 mg (1.72 mmol) of ethyl 3-{3-[3-(5-carboxypentyloxy)-5,5,8,8-tetramethyl-5,6,7,8-tetrahydro-2-naphthyl]-4-methoxyphenyl}acrylate obtained above, 647 mg (76%) of the expected compound were obtained in the form of a white powder having a melting point of 166°–168° C.

Example 25

Synthesis of 3-{3-[3-(5-Carbamoylpentyloxy)-5,5,8,8-tetramethyl-5,6,7,8-tetrahydro-2-naphthyl]-4-methoxyphenyl}acrylic Acid (a) Preparation of Ethyl 3-{3-[3-(5-Carbamoylpentyloxy)-5,5,8,8-tetramethyl-5,6,7,8-tetrahydro-2-naphthyl]-4-methoxyphenyl}acrylate:

A solution of 1.27 g (2.43 mmol) of ethyl 3-{3-[3-(5-carboxypentyloxy)-5,5,8,8-tetramethyl-5,6,7,8-tetrahydro-2-naphthyl]-4-methoxyphenyl}acrylate obtained in Example 24(a) dissolved in 35 ml of dichloromethane was introduced into a round-bottomed flask, 505 μl (2.55 mmol) of dicyclohexylamine were added, and the mixture was stirred for 10 minutes. Then 186 μl (2.55 mmol) of thionyl chloride were added dropwise and the mixture was stirred at room temperature for 10 minutes. The reaction medium was evaporated to dryness, the residue obtained was taken up in ethyl ether, the suspension was filtered and the filtrate was evaporated. The residue obtained was dissolved in 15 ml of THF and the solution was introduced dropwise under nitrogen into a three-necked flask containing 20 ml of THF, 405 μl (2.92 mmol) of triethylamine and 160 μl of a 34% aqueous ammonia solution (2.67 mmol). The mixture was stirred at room temperature for 30 minutes, the reaction medium was poured into water, acidified to a pH of 1 with 1N hydrochloric acid and extracted with ethyl ether, and the organic phase was decanted, dried over magnesium sulfate, filtered and evaporated. The residue obtained was purified by chromatography on a silica column eluted with a mixture of heptane and ethyl acetate (80:20). After evaporation of the solvents, 750 mg (60%) of the expected compound were obtained in the form of a white powder having a melting point of 133°–135° C.

(b) Synthesis of 3-{3-[3-(5-Carbamoylpentyloxy)-5,5,8,8-tetramethyl-5,6,7,8-tetrahydro-2-naphthyl]-4-methoxyphenyl}acrylic Acid:

In a manner similar to that of Example 2(h), starting from 900 mg (1.4 mmol) of ethyl 3-{3-[3-(5-carbamoylpentyloxy)-5,5,8,8-tetramethyl-5,6,7,8-tetrahydro-2-naphthyl]-4-methoxyphenyl}acrylate obtained above, 190 mg (27%) of the expected compound were obtained in the form of a white powder having a melting point of 179°–181° C.

Example 26

Synthesis of 3-{3-[3-(7-Carbamoylheptyloxy)-5,5,8,8-tetramethyl-5,6,7,8-tetrahydro-2-naphthyl]-4-methoxyphenyl}acrylic Acid (a) Preparation of Ethyl 3-{3-[3-(7-Carbamoylpentyloxy)-5,5,8,8-tetramethyl-5,6,7,8-tetrahydro-2-naphthyl]-4-methoxyphenyl}acrylate:

In a manner similar to that of Example 25(a), starting from 1.5 g (2.70 mmol) of ethyl 3-{3-[3-(7-Carboxyheptyloxy)-5,5,8,8-tetramethyl-5,6,7,8-tetrahydro-2-naphthyl]-4-methoxyphenyl}acrylate obtained in Example 23(a), 1 g (68%) of the expected compound was obtained in the form of a beige powder having a melting point of 132°–134° C.

(b) Synthesis of 3-{3-[3-(7-Carbamoylheptyloxy)-5,5,8,8-tetramethyl-5,6,7,8-tetrahydro-2-naphthyl]-4-methoxyphenyl}acrylic Acid:

In a manner similar to that of Example 2(h), starting from 1 g (1.8 mmol) of ethyl 3-{3-[3-(7-carbamoylheptyloxy)-5,5,8,8-tetramethyl-5,6,7,8-tetrahydro-2-naphthyl]-4-methoxyphenyl}acrylate obtained above, 700 mg (74%) of the expected compound were obtained in the form of a white powder having a melting point of 199°201° C.

Example 27

Synthesis of 3-{4-Methoxy-3-[5,5,8,8-tetramethyl-3-(2-morpholin-4-yl-ethoxy)-5,6,7,8-tetrahydro-2-naphthyl]phenyl}acrylic Acid (a) Preparation of Ethyl 3-{4-Methoxy-3-[5,5,8,8-tetramethyl-3-(2-morpholin-4-yl-ethoxy)-5,6,7,8-tetrahydro-2-naphthyl]phenyl}acrylate:

In a manner similar to that of Example 16(a), by reaction of 1.4 g (3.4 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 760 mg (4.08 mmol) of 4-(2-chloroethyl)morpholine hydrochloride, 1.5 g (85%) of the expected compound was obtained in the form of a yellow oil.

$^1$H NMR (CDCl$_3$): 1.27 (s, 6H), 1.29 to 1.35 (m, 9H), 1.70 (s, 4H), 2.37 (m, 4H), 2.60 (t, J=5.75 Hz, 2H), 3.59 (m, 4H), 3.81 (s, 3H), 4.05 (t, J=5.50 Hz, 2H), 4.25 (q, J=7.0 Hz, 2H), 6.30 (d, J=15.75 Hz, 1H), 6.85 (s, 1H), 6.91 to 6.95 (m, 1H), 7.16 (s, 1H), 7.44 to 7.49 (m, 2H), 7.65 (d, J=16.0 Hz, 1H).

(b) Synthesis of 3-{4-Methoxy-3-[5,5,8,8-tetramethyl-3-(2-morpholin-4-yl-ethoxy)-5,6,7,8-tetrahydro-2-naphthyl]phenyl}-acrylic Acid:

In a manner similar to that of Example 2(h), starting from 1.5 g (2.9 mmol) of ethyl 3-{4-methoxy-3-[5,5,8,8-tetramethyl-3-(2-morpholin-4-yl-ethoxy)-5,6,7,8-tetrahydro-2-naphthyl]phenyl}acrylate obtained above, 1.17 g (83%) of the expected compound was obtained in the form of a white powder which decomposed commencing at 140° C.

¹H NMR (CD₃OD (Ref.: q at δ=2.85 ppm)): 0.79 (s, 6H), 0.87 (s, 6H), 1.26 (s, 4H), 1.90 (m, 4H), 2.18 (t, J=5.0 Hz, 2H), 3.07 (m, 4H), 3.31 (s, 3H), 3.61 (t, J=5.0 Hz, 2H), 5.91 (d, J=15.75 Hz, 1H), 6.45 (s, 1H), 6.56 (d, J=8.5 Hz, 1H), 6.62 (s, 1H), 6.87 (d, J=1.75 Hz, 1H), 7.01 to 7.09 (m, 2H).

Example 28

Synthesis of 3-{4-Methoxy-3-[5,5,8,8-tetramethyl-3-(2-piperidin-1-yl-ethoxy)-5,6,7,8-tetrahydro-2-naphthyl]phenyl}acrylic Acid (a) Preparation of Ethyl 3-{4-Methoxy-3-[5,5,8,8-tetramethyl-3-(2-piperidin-1-yl-ethoxy)-5,6,7,8-tetrahydro-2-naphthyl]phenyl}acrylate:

In a manner similar to that of Example 16(a), by reaction of 1.4 g (3.4 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) and 760 mg (4.08 mmol) of 1-(2-chloroethyl)piperidine hydrochloride, 1.57 g (89%) of the expected compound was obtained in the form of a colorless oil.

¹H NMR (CDCl₃): 1.22 to 1.38 (m, 16H), 1.46 to 1.55 (m, 4H), 1.69 (m, 5H), 2.36 (m, 4H), 2.60 (t, J=6.25 Hz, 2H), 3.81 (s, 3H), 4.05 (t, J=6.0 Hz, 2H), 4.24 (q, J=7.25 Hz, 2H), 6.30 (d, J=16.0 Hz, 1H), 6.85 (s, 1H), 6.93 (d, J=9.25 Hz, 1H), 7.16 (s, 1H), 7.44 to 7.48 (m, 2H), 7.66 (d, J=16.0 Hz, 1H).

(b) Synthesis of 3-{4-Methoxy-3-[5,5,8,8-tetramethyl-3-(2-piperidin-1-yl-ethoxy)-5,6,7,8-tetrahydro-2-naphthyl]phenyl}acrylic Acid:

In a manner similar to that of Example 2(h), starting from 1.57 g (3 mmol) of ethyl 3-{4-methoxy-3-[5,5,8,8-tetramethyl-3-(2-piperidin-1-yl-ethoxy)-5,6,7,8-tetrahydro-2-naphthyl]phenyl}acrylate obtained above, 900 mg (61%) of the expected compound were obtained in the form of a white powder having a melting point of 251°–253° C.

Example 29

Synthesis of 3-{4-Methoxy-3-[3-(2-methoxymethoxybenzyloxy)-5,5,8,8-tetramethyl-5,6,7,8-tetrahydro-2-naphthyl]phenyl}acrylic Acid (a) Preparation of 2-Methoxymethoxybenzaldehyde:

In a manner similar to that of Example 1(a), by reaction of 30 g (245 mmol) of 2-hydroxybenzaldehyde with 21 ml (270 mmol) of methoxymethyl chloride, 40.7 g (100%) of the expected compound were obtained in the form of an off-white oil.

¹H NMR (CDCl₃): 3.53 (s, 3H), 5.31 (s, 2H), 7.09 (t, J=7.5 Hz, 1H), 7.22 (d, J=8.25 Hz, 1H), 7.50 to 7.57 (m, 1H), 7.85 (dd, J1=7.75 Hz, J2=1.75 Hz, 1H), 10.51 (s, 1H).

(b) Preparation of (2-Methoxymethoxyphenyl)methanol:

A solution of 40 g (241 mmol) of 2-methoxymethoxybenzaldehyde dissolved in 250 ml of THF was introduced under a stream of nitrogen into a 2-liter round-bottom flask, and 3.65 g (96 mmol) of lithium aluminum hydride were added in small portions. The reaction medium was stirred at room temperature for 15 minutes, before being hydrolyzed slowly with a saturated ammonium chloride solution and was then acidified to a pH of 1 with a 1N hydrochloric acid solution. The reaction medium was extracted with ethyl acetate, the organic phase was decanted, dried over magnesium sulfate and filtered, and the filtrate was evaporated. 39.2 g (96%) of a colorless oil were collected.

¹H NMR (CDCl₃): 2.29 (m, 1H), 3.49 (s, 3H), 4.80 (d, J=6.0 Hz, 2H), 5.25 (s, 2H), 6.98 to 7.12 (m, 2H), 7.23 to 7.34 (m, 2H).

(c) Preparation of 2-Methoxymethoxybenzyl Chloride:

5.0 g (29.7 mmol) of (2-methoxymethoxyphenyl)methanol obtained above, 90 ml of dichloromethane and 8.27 ml (59.5 mmol) of triethylamine were introduced in succession under a stream of nitrogen into a 250 ml three-necked flask. Then 2.76 g (35.7 mmol) of methanesulfonyl chloride were added dropwise and the mixture was stirred at room temperature for 1 hour. The reaction medium was hydrolyzed with hydrochloric acid and extracted with dichloromethane, the organic phase was dried over magnesium sulfate and filtered, and the filtrate was evaporated. The orange oil obtained was purified by chromatography on a silica column eluted with a mixture of ethyl acetate and heptane (1:9). After evaporation of the solvents, 3.0 g (55%) of the expected compound in the form of a yellow oil were collected.

¹H NMR (CDCl₃): 3.50 (s, 3H), 4.67 (s, 2H), 3.25 (s, 2H), 6.99 (td, J1=7.5 Hz, J2=1.0 Hz, 1H), 7.11 (d, J=7.75 Hz, 1H), 7.24 to 7.38 (m, 2H).

(d) Preparation of Ethyl 3-{4-Methoxy-3-[3-(2-methoxymethoxybenzyloxy)-5,5,8,8-tetramethyl-5,6,7,8-tetrahydro-2-naphthyl]phenyl}acrylate:

In a manner similar to that of Example 1(a), by reaction of 2.5 g (6.12 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 1.26 g (6.73 mmol) of 2-methoxymethoxybenzyl chloride obtained above, 3.2 g (94%) of the expected compound were obtained in the form of a yellow oil.

¹H NMR (CDCl₃): 1.27 to 1.35 (m, 15H), 1.69 (s, 4H), 3.43 (s, 3H), 3.74 (s, 3H), 4.25 (q, J=7.0 Hz, 2H), 5.07 (s, 2H), 5.18 (s, 2H), 6.29 (d, J=16.0 Hz, 1H), 6.90 to 6.95 (m, 3H), 7.06 (d, J=7.5 Hz, 1H), 7.15 to 7.21 (m, 3H), 7.47 (dd, J1=8.5 Hz, J2=2.25 Hz, 1H), 7.52 (d, J=2.25 Hz, 1H), 7.66 (d, J=16.0 Hz, 1H)

(e) Synthesis of 3-{4-methoxy-3-[3-(2-methoxymethoxybenzyloxy)-5,5,8,8-tetramethyl-5,6,7,8-tetrahydro-2-naphthyl]phenyl}acrylic Acid:

In a manner similar to that of Example 2(h), starting from 1.0 g (1.8 mmol) of ethyl 3-{4-methoxy-3-[3-(2-methoxymethoxybenzyloxy)-5,5,8,8-tetramethyl-5,6,7,8-tetrahydro-2-naphthyl]phenyl}acrylate obtained above, 760 mg (80%) of the expected compound were obtained in the form of a white powder having a melting point of 159°–161° C.

Example 30

Synthesis of 3-{4-Methoxy-3-[3-(3-methoxymethoxybenzyloxy)-5,5,8,8-tetramethyl-5,6,7,8-tetrahydro-2-naphthyl]phenyl}acrylic Acid (a) Preparation of 3-Methoxymethoxybenzaldehyde:

In a manner similar to that of Example 1(a), by reaction of 30 g (245 mmol) of 3-hydroxybenzaldehyde with 21 ml (270 mmol) of methoxymethyl chloride, 40.7 g (100%) of the expected compound were obtained in the form of a chestnut-brown oil.

¹H NMR (CDCl₃): 3.49 (s, 3H), 5.23 (s, 2H), 7.27 to 7.32 (m, 1H), 7.42 to 7.55 (m, 3H), 9.97 (s, 1H).

(b) Preparation of (3-Methoxymethoxyphenyl)methanol:

In a manner similar to that of Example 29(b), by reaction of 40 g (240 mmol) of 3-methoxymethoxybenzaldehyde with 3.65 g (96 mmol) of lithium aluminum hydride, 40.7 g (100%) of the expected compound were obtained in the form of a colorless oil.

¹H NMR (CDCl₃): 1.83 (br, 1H), 3.48 (s, 3H), 4.67 (s, 2H), 5.18 (s, 2H), 6.94 to 7.06 (m, 3H), 7.24 to 7.31 (m, 1H).

(c) Preparation of 3-Methoxymethoxybenzyl Chloride:

In a manner similar to that of Example 29(c), by reaction of 5.0 g (29.7 mmol) of (3-methoxymethoxyphenyl) methanol with 8.27 ml (59.5 mmol) of triethylamine and 2.76 ml (35.7 mmol) of methanesulfonyl chloride, 2.66 g (48%) of the expected compound were obtained in the form of a yellow oil.

$^1$H NMR (CDCl$_3$): 3.48 (s, 3H), 4.55 (s, 2H), 5.22 (s, 2H), 6.97 to 7.07 (m, 3H), 7.24 to 7.30 (m, 1H).

(d) Preparation of Ethyl 3-{4-methoxy-3-[3-(3-methoxymethoxybenzyloxy)-5,5,8,8-tetramethyl-5,6,7,8-tetrahydro-2-naphthyl]phenyl}acrylate:

In a manner similar to that of Example 1(a), by reaction of 2.5 g (6.12 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 1.26 g (6.73 mmol) of 3-methoxymethoxybenzyl chloride obtained above, 2.90 g (85%) of the expected compound were obtained in the form of a yellow oil.

$^1$H NMR (CDCl$_3$): 1.27 to 1.35 (m, 15H), 1.69 (s, 4H), 3.43 (s, 3H), 3.77 (s, 3H), 4.24 (q, J=7.25 Hz, 2H), 4.99 (s, 2H), 5.09 (s, 2H), 6.31 (d, J=15.75 Hz, 1H), 6.88 to 6.96 (m, 5H), 7.16 to 7.23 (m, 2H), 7.45 to 7.51 (m, 2H), 7.67 (d, J=15.75 Hz, 1H).

(e) Synthesis of 3-{4-Methoxy-3-[3-(3-methoxymethoxybenzyloxy)-5,5,8,8-tetramethyl-5,6,7,8-tetrahydro-2-naphthyl]phenyl}acrylic Acid:

In a manner similar to that of Example 2(h), starting from 1.0 g (1.79 mmol) of ethyl 3-{4-methoxy-3-[3-(3-methoxymethoxybenzyloxy)-5,5,8,8-tetramethyl-5,6,7,8-tetrahydro-2-naphthyl]phenyl}acrylate obtained above, 813 mg (85%) of the expected compound were obtained in the form of a white powder having a melting point of 144°–146° C.

Example 31

Synthesis of 3-{4-Methoxy-3-[3-(4-methoxymethoxybenzyloxy)-5,5,8,8-tetramethyl-5,6,7,8-tetrahydro-2-naphthyl]phenyl}acrylic Acid (a) Preparation of 4-Methoxymethoxybenzaldehyde:

In a manner similar to that of Example 1(a), by reaction of 30 g (245 mmol) of 4-hydroxybenzaldehyde with 21 ml (270 mmol) of methoxymethyl chloride, 40.7 g (100%) of the expected compound were obtained in the form of an orange oil.

$^1$H NMR (CDCl$_3$): 3.49 (s, 3H), 5.28 (s, 2H), 7.15 (d, J=8.75 Hz, 2H), 7.84 (d, J=8.75 Hz, 2H), 9.9 (s, 1H), (b) Preparation of (4-Methoxymethoxyphenyl)methanol:

In a manner similar to that of Example 29(b), by reaction of 40 g (240 mmol) of 4-methoxymethoxybenzaldehyde with 3.65 g (96 mmol) of lithium aluminum hydride, 15 g (37%) of the expected compound were obtained in the form of a colorless oil.

$^1$H NMR (CDCl$_3$): 1.71 (t, J=5.75 Hz, 1H), 3.47 (s, 3H), 4.61 (d, J=5.75 Hz, 2H), 5.17 (s, 2H), 7.02 (d, J=8.5 Hz, 2H), 7.29 (d, J=8.5 Hz, 2H).

(c) Preparation of 4-Methoxymethoxybenzyl Chloride:

In a manner similar to that of Example 29(c), by reaction of 5.0 g (29.7 mmol) of (4-methoxymethoxyphenyl) methanol with 8.27 ml (59.5 mmol) of triethylamine and 2.76 ml (35.7 mmol) of methanesulfonyl chloride, 2.66 g (48%) of the expected compound were obtained in the form of a yellow oil.

$^1$H NMR (CDCl$_3$): 3.47 (s, 3H), 4.56 (s, 2H), 5.17 (s, 2H), 7.02 (d, J=8.75 Hz, 2H), 7.31 (d, J=8.75 Hz, 2H).

(d) Preparation of Ethyl 3-{4-methoxy-3-[3-(4-methoxymethoxybenzyloxy)-5,5,8,8-tetramethyl-5,6,7,8-tetrahydro-2-naphthyl]phenyl}acrylate:

In a manner similar to that of Example 1(a), by reaction of 2.5 g (6.12 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 1.26 g (6.73 mmol) of 4-methoxymethoxybenzyl chloride obtained above, 3.0 g (87%) of the expected compound were obtained in the form of a white powder having a melting point of 106°–108° C.

(e) Synthesis of 3-{4-Methoxy-3-[3-(4-methoxymethoxybenzyloxy)-5,5,8,8-tetramethyl-5,6,7,8-tetrahydro-2-naphthyl]phenyl}acrylic Acid:

In a manner similar to that of Example 2(h), starting from 1.0 g (1.79 mmol) of ethyl 3-{4-methoxy-3-[3-(4-methoxymethoxybenzyloxy)-5,5,8,8-tetramethyl-5,6,7,8-tetrahydro-2-naphthyl]phenyl}acrylate obtained above, 877 mg (91%) of the expected compound were obtained in the form of a white powder having a melting point of 184°–186° C.

Example 32

Synthesis of 3-{4-Methoxy-3-[3-(3-hydroxybenzyloxy)-5,5,8,8-tetramethyl-5,6,7,8-tetrahydro-2-naphthyl]phenyl}acrylic Acid (a) Preparation of Ethyl 3-{4-Methoxy-3-[3-(3-hydroxybenzyloxy)-5,5,8,8-tetramethyl-5,6,7,8-tetrahydro-2-naphthyl]phenyl}acrylate:

In a manner similar to that of Example 2(g) but in ethanol as solvent, starting from 1.9 g (3.4 mmol) of ethyl 3-{4-methoxy-3-[3-(3-methoxymethoxybenzyloxy)-5,5,8,8-tetramethyl-5,6,7,8-tetrahydro-2-naphthyl]phenyl}acrylate obtained in Example 30(d), 1.38 g (79%) of the expected compound was obtained in the form of a white powder having a melting point of 131°–133° C.

(b) Synthesis of 3-{4-Methoxy-3-[3-(3-hydroxybenzyloxy)-5,5,8,8-tetramethyl-5,6,7,8-tetrahydro-2-naphthyl]phenyl}acrylic Acid:

In a manner similar to that of Example 2(h), starting from 1.11 g (2.16 mmol) of ethyl 3-{4-methoxy-3-[3-(3-hydroxybenzyloxy)-5,5,8,8-tetramethyl-5,6,7,8-tetrahydro-2-naphthyl]phenyl}acrylate obtained above, 1.0 g (95%) of the expected compound was obtained in the form of a white powder having a melting point of 229°–231° C.

Example 33

Synthesis of 3-[4-Fluoro-3-(3,5,5,8,8-pentamethyl-5,6,7,8-tetrahydro-2-naphthyl)phenyl]acrylic Acid In a manner similar to that of Example 1(c), by reaction of 2.0 g (8.12 mmol) of 3,5,5,8,8-pentamethyl-5,6,7,8-tetrahydro-2-naphthylboronic acid (prepared in Example 5(a) of the patent WO-97/33881) and 1.54 g (6.25 mmol) of 3-(3-bromo-4-fluorophenyl)acrylic acid, 1.45 g (63%) of the expected compound was obtained in the form of a beige powder having a melting point of 181°–183° C.

Example 34

Synthesis of 3-{4-Hydroxy-3-[3-(3-methoxybenzyloxy)-5,5,8,8-tetramethyl-5,6,7,8-tetrahydro-2-naphthyl]phenyl}acrylic Acid (a) Preparation of 2-Bromo-3-(3-methoxybenzyloxy)-5,5,8,8-tetramethyl-5,6,7,8-tetrahydronaphthalene:

In a manner similar to that of Example 1(a), by reaction of 5.0 g (17.7 mmol) of 2-bromo-3-hydroxy-5,5,8,8- tetramethyl-5,6,7,8-tetrahydronaphthalene with 3.0 g (19.4 mmol) of 3-methoxybenzyl chloride, 7.14 g (100%) of the expected compound were obtained in the form of a chestnut-brown oil.

$^1$H NMR (CDCl$_3$): 1.21 (s, 6H), 1.24 (s, 6H), 1.64 (s, 4H), 3.82 (s, 3H), 5.09 (s, 2H), 6.83 to 6.87 (m, 2H), 7.03 to 7.08 (m, 2H), 7.29 (m, 1H), 7.43 (s, 1H).

(b) Preparation of 3-(3-Methoxybenzyloxy)-5,5,8,8-tetramethyl-5,6,7,8-tetrahydro-2-naphthylboronic Acid:

In a manner similar to that of Example 1(b), starting from 7.10 g (17.6 mmol) of 2-bromo-3-(3-methoxybenzyloxy)-5,5,8,8-tetramethyl-5,6,7,8-tetrahydronaphthalene obtained above, 4.85 g (74%) of the expected compound were obtained in the form of a slightly tacky beige powder.

$^1$H NMR (CDCl$_3$): 1.26 (s, 6H), 1.29 (s, 6H), 1.67 (s, 4H), 3.81 (s, 3H), 5.06 (s, 2H), 6.85 to 7.0 (m, 3H), 7.31 (t, J=7.75 Hz, 1H), 7.78 (s, 1H).

(c) Preparation of Ethyl 3-(3-Bromo-4-methoxymethoxyphenyl)acrylate:

In a manner similar to that of Example 2(c), by reaction of 30 g (122 mmol) of ethyl 3-(3-bromo-4-methoxymethoxyphenyl)acrylate obtained above with 30.27 g (135 mmol) of triethyl phosphonoacetate, 34.6 g (90%) of the expected compound were obtained in the form of white crystals having a melting point of 64°–66° C.

(d) Preparation of Ethyl 3-(3-Bromo-4-hydroxyphenyl) acrylate:

In a manner similar to that of Example 2(g), starting from 30 g (95 mmol) of ethyl 3-(3-bromo-4-methoxymethoxyphenyl)acrylate obtained above, 25.8 g (100%) of the expected compound were obtained in the form of a white powder having a melting point of 113°–115° C.

(e) Preparation of Ethyl 3-{4-Hydroxy-3-[3-(3-methoxybenzyloxy)-5,5,8,8-tetramethyl-5,6,7,8-tetrahydro-2-naphthyl]phenyl}acrylate:

In a manner similar to that of Example 1(c), by reaction of 1.0 g (3.7 mmol) of ethyl 3-(3-bromo-4-hydroxyphenyl) acrylate obtained above with 1.77 g (4.8 mmol) of 3-(3-methoxybenzyloxy)-5,5,8,8-tetramethyl-5,6,7,8-tetrahydro-2-naphthylboronic acid obtained in Example 34(c), 630 mg (33%) of the expected compound were obtained in the form of a colorless oil.

$^1$H NMR (CDCl$_3$): 1.25 to 1.36 (m, 15H), 1.70 (s, 4H), 3.78 (s, 3H), 4.26 (q, J=7.25 Hz, 2H), 4.99 (s, 2H), 6.32 (d, J=15.75 Hz, 1H), 6.84 (d, J=8.5 Hz, 2H), 6.93 (s, 1H), 6.98 to 7.02 (m, 2H), 7.19 (d, J=8.5 Hz, 1H), 7.25 (s, 1H), 7.40 (d, J=2.25 Hz, 1H), 7.69 (d, J=15.75 Hz, 1H).

(f) Synthesis of 3-{4-Hydroxy-3-[3-(3-methoxybenzyloxy)-5,5,8,8-tetramethyl-5,6,7,8-tetrahydro-2-naphthyl]phenyl}-acrylic acid:

In a manner similar to that of Example 2(h), starting from 600 mg (1.16 mmol) of ethyl 3-{4-hydroxy-3-[3-(3-methoxybenzyloxy)-5,5,8,8-tetramethyl-5,6,7,8-tetrahydro-2-naphthyl]phenyl}acrylate obtained above, 539 mg (95%) of the expected compound were obtained in the form of a white powder having a melting point of 197°–199° C.

Example 35

Synthesis of 3-{4-hydroxy-3-[3-(4-methoxybenzyloxy)-5,5,8,8-tetramethyl-5,6,7,8-tetrahydro-2-naphthyl]phenyl}acrylic Acid (a) Preparation of 2-Bromo-3-(4-methoxybenzyloxy)-5,5,8,8-tetramethyl-5,6,7,8-tetrahydronaphthalene:

In a manner similar to that of Example 1(a), by reaction of 5.0 g (17.7 mmol) of 3-hydroxy-2-bromo-5,5,8,8-tetramethyl-5,6,7,8-tetrahydronaphthalene with 3.0 g (19.4 mmol) of 4-methoxybenzyl chloride, 7.14 g (100%) of the expected compound were obtained in the form of a chestnut-brown oil.

$^1$H NMR (CDCl$_3$): 1.21 (s, 6h), 1.24 (s, 6H), 1.64 (s, 4H), 3.81 (s, 3H), 5.04 (s, 2H), 6.83 (s, 1H), 6.92 (d, J=7.5 Hz, 2H), 7.39 (d, J=7.5 Hz, 2H), 7.43 (s, 1H).

(b) Preparation of 3-(4-Methoxybenzyloxy)-5,5,8,8-tetramethyl-5,6,7,8-tetrahydro-2-naphthylboronic Acid:

In a manner similar to that of Example 1(b), starting from 7.14 g (17.7 mmol) of 2-bromo-3-(4-methoxybenzyloxy)-5,5,8,8-tetramethyl-5,6,7,8-tetrahydronaphthalene obtained above, 3.55 g (54%) of the expected compound were obtained in the form of an orange oil.

$^1$H (CDCl$_3$): 1.28 (s, 12H), 1.57 (s, 4H), 3.82 (s, 3H), 5.03 (s, 2H), 5.78 (s, 2H), 6.89 (s, 1H), 6.93 (d, J=8.75 Hz, 1H), 7.35 (d, J=8.5 Hz, 1H), 7.78 (s, 1H).

(c) Preparation of Ethyl 3-{4-Hydroxy-3-[3-(4-methoxybenzyloxy)-5,5,8,8-tetramethyl-5,6,7,8-tetrahydro-2-naphthyl]phenyl}acrylate:

In a manner similar to that of Example 1(c), by reaction of 1.0 g (3.7 mmol) of ethyl 3-(3-bromo-4-hydroxyphenyl) acrylate obtained in Example 34(d) with 2.0 g (5.5 mmol) of 3-(4-methoxybenzyloxy)-5,5,8,8-tetramethyl-5,6,7,8-tetrahydro-2-naphthylboronic acid obtained above, 930 mg (49%) of the expected compound were obtained in the form of a colorless oil.

$^1$H NMR (CDCl$_3$): 1.29 (s, 12H), 1.34 (t, J=7.0 Hz, 3H), 1.70 (s, 4H), 3.72 (s, 3H), 4.26 (q, J=7.25 Hz, 2H), 5.02 (s, 2H), 6.33 (d, J=15.75 Hz, 1H), 6.70 (s, 1H), 6.80 to 6.87 (m, 3H), 7.02 (d, J=7.25 Hz, 2H), 7.18 to 7.25 (m, 2H), 7.42 (d, J=2.25 Hz, 1H), 7.48 (d, J=8.5 Hz, 1H), 7.69 (d, J=16.0 Hz, 1H).

(d) Synthesis of 3-{4-Hydroxy-3-[3-(3-methoxybenzyloxy)-5,5,8,8-tetramethyl-5,6,7,8-tetrahydro-2-naphthyl] phenyl}acrylic Acid:

In a manner similar to that of Example 2(h), starting from 930 mg (1.8 mmol) of ethyl 3-{4-hydroxy-3-[3-(4-methoxybenzyloxy)-5,5,8,8-tetramethyl-5,6,7,8-tetrahydro-2-naphthyl]phenyl}acrylate obtained above, 800 mg (91%) of the expected compound were obtained in the form of a white powder having a melting point of 170°–172°C.

Example 36

Synthesis of 3-{4-Hydroxy-3-[3-(4-fluorobenzyloxy)-5,5,8,8-tetramethyl-5,6,7,8-tetrahydro-2-naphthyl]phenyl}acrylic Acid (a) Preparation of 2-bromo-3-(4-fluorobenzyloxy)-5,5,8,8-tetramethyl-5,6,7,8-tetrahydronaphthalene:

In a manner similar to that of Example 1(a), by reaction of 5.0 g (17.7 mmol) of 3-hydroxy-2-bromo-5,5,8,8-tetramethyl-5,6,7,8-tetrahydronaphthalene with 3.67 g (19.4 mmol) of 4-fluorobenzyl bromide, 4.3 g (62%) of the expected compound were obtained in the form of light chestnut-brown crystals having a melting point of 74°–76° C.

(b) Preparation of 3-(4-Fluorobenzyloxy)-5,5,8,8-tetramethyl-5,6,7,8-tetrahydro-2-naphthylboronic Acid:

In a manner similar to that of Example 1(b), starting from 4.3 g (11.0 mmol) of 2-bromo-3-(4-fluorobenzyloxy)-5,5,8,8-tetramethyl-5,6,7,8-tetrahydronaphthalene obtained above, 3.24 g (83%) of the expected compound were obtained in the form of an orange oil.

$^1$H NMR (CDCl$_3$): 1.27 (s, 6H), 1.29 (s, 6H), 1.67 (s, 4H), 5.08 (s, 2H), 5.81 (s, 2H), 7.06 to 7.13 (m, 2H), 7.38 to 7.43 (m, 2H), 7.80 (s, 1H).

(c) Preparation of Ethyl 3-{4-Hydroxy-3-[3-(4-fluorobenzyloxy)-5,5,8,8-tetramethyl-5,6,7,8-tetrahydro-2-naphthyl]phenyl}acrylate:

In a manner similar of Example 1(c), by reaction of 1.0 g (3.7 mmol) of ethyl 3-(3-bromo-4-hydroxyphenyl)acrylate obtained in Example 34(d) with 1.97 g (5.5 mmol) of 3-(4-fluorobenzyloxy)-5,5,8,8-tetramethyl-5,6,7,8-tetrahydro-2-naphthylboronic acid obtained above, 825 mg (44%) of the expected compound were obtained in the form of a white solid having a melting point of 123°–125° C.

(d) Synthesis of 3-{4-Hydroxy-3-[3-(3-fluorobenzyloxy)-5,5,8,8-tetramethyl-5,6,7,8-tetrahydro-2-naphthyl]phenyl}acrylic Acid:

In a manner similar to that of Example 2(h), starting from 800 mg (1.6 mmol) of ethyl 3-{4-hydroxy-3-[3-(4-fluorobenzyloxy)-5,5,8,8-tetramethyl-5,6,7,8-tetrahydro-2-naphthyl]phenyl]acrylate obtained above, 425 mg (56%) of the expected compound were obtained in the form of a white powder having a melting point of 157°–159° C.

Example 37

Synthesis of 3-{4-Hydroxy-3-[3-(4-chlorobenzyloxy)-5,5,8,8-tetramethyl-5,6,7,8-tetrahydro-2-naphthyl]phenyl}acrylic Acid (a) Preparation of 2-Bromo-3-(4-chlorobenzyloxy)-5,5,8,8-tetramethyl-5,6,7,8-tetrahydronaphthalene:

In a manner similar to that of Example 1(a), by reaction of 5.0 g (17.7 mmol) of 3-hydroxy-2-bromo-5,5,8,8-tetramethyl-5,6,7,8-tetrahydronaphthalene with 3.12 g (19.4 mmol) of 4-chlorobenzyl chloride, 7.22 g (100%) of the expected compound were obtained in the form of pale chestnut-brown crystals having a melting point of 108°–110° C.

(b) Preparation of 3-(4-Chlorobenzyloxy)-5,5,8,8-tetramethyl-5,6,7,8-tetrahydro-2-naphthylboronic Acid:

In a manner similar to that of Example 1(b), starting from 7.14 g (17.5 mmol) of 2-bromo-3-(4-chlorobenzyloxy)-5,5,8,8-tetramethyl-5,6,7,8-tetrahydronaphthalene obtained above, 3.50 g (54%) of the expected compound were obtained in the form of an orange oil.

$^1$H NMR (CDCl$_3$): 1.26 (s, 6H), 1.29 (s, 6H), 1.67 (s, 4H), 5.09 (s, 2H), 5.72 (s, 2H), 6.84 (s, 1H), 7.37 (m, 4H), 7.80 (s, 1H).

(c) Preparation of Ethyl 3-{4-Hydroxy-3-[3-(4-chlorobenzyloxy)-5,5,8,8-tetramethyl-5,6,7,8-tetrahydro-2-naphthyl]phenyl}acrylate:

In a manner similar to that of Example 1(c), by reaction of 1.0 g (3.7 mmol) of ethyl 3-(3-bromo-4-hydroxyphenyl)acrylate obtained in Example 34(d) with 2.05 g (5.5 mmol) of 3-(4-chlorobenzyloxy)-5,5,8,8-tetramethyl-5,6,7,8-tetrahydro-2-naphthylboronic acid obtained above, 590 mg (30%) of the expected compound were obtained in the form of a white solid having a melting point of 152°–154° C.

(d) Synthesis of 3-{4-Hydroxy-3-[3-(4-chlorobenzyloxy)-5,5,8,8-tetramethyl-5,6,7,8-tetrahydro-2-naphthyl]phenyl}acrylic Acid:

In a manner similar to that of Example 2(h), starting from 580 mg (1.12 mmol) of ethyl 3-{4-hydroxy-3-[3-(4-chlorobenzyloxy)-5,5,8,8-tetramethyl-5,6,7,8-tetrahydro-2-naphthyl]phenyl}acrylate obtained above, 382 mg (70%) of the expected compound were obtained in the form of a white powder having a melting point of 147°–149° C.

Example 38

Synthesis of 3-[4-Hydroxy-3-(3-methoxymethoxy-5,5,8,8-tetramethyl-5,6,7,8-tetrahydro-2-naphthyl)phenyl]acrylic Acid (a) Preparation of Ethyl 3-(4-Hydroxy-3-[3-methoxymethoxy-5,5,8,8-tetramethyl-5,6,7,8-tetrahydro-2-naphthyl]phenyl}acrylate:

In a manner similar to that of Example 1(c), by reaction of 1.0 g (3.7 mmol) of ethyl 3-(3-bromo-4-hydroxyphenyl)acrylate obtained in Example 34(d) with 1.6 g (5.5 mmol) of 3-methoxymethoxy-5,5,8,8-tetramethyl-5,6,7,8-tetrahydro-2-naphthylboronic acid obtained in Example 13(b), 150 mg (9%) of the expected compound were obtained in the form of a white solid having a melting point of 101°–103° C.

(b) Synthesis of 3-{4-Hydroxy-3-[3-methoxymethoxy-5,5,8,8-tetramethyl-5,6,7,8-tetrahydro-2-naphthyl]phenyl}acrylic Acid:

In a manner similar to that of Example 2(h), starting from 150 mg (0.34 mmol) of ethyl 3-{4-hydroxy-3-[3-methoxymethoxy-5,5,8,8-tetramethyl-5,6,7,8-tetrahydro-2-naphthyl]phenyl}acrylate obtained above, 100 mg (72%) of the expected compound were obtained in the form of a white powder having a melting point of 191°–193° C.

Example 39

Synthesis of 3-(3',5'-di-tert-Butyl-6-hydroxy-2'-propyloxy-3-biphenylyl)acrylic Acid (a) Preparation of 1-Bromo-3,5-di-tert-butyl-2-propyloxybenzene:

In a manner similar to that of Example 1(a), by reaction of 15 g (52.6 mmol) of 6-bromo-2,4-di-tert-butylphenol with 7.4 g (57.9 mmol) of 1-bromopropane, 17.2 g (100%) of the expected compound were obtained in the form of orange crystals having a melting point of 41°–43° C.

(b) Preparation of 2-Propyloxy-3,5-di-tert-butylphenylboronic Acid:

In a manner similar to that of Example 1(b), starting from 16.0 g (48.9 mmol) of 1-bromo-3,5-di-tert-butyl-2-propyloxybenzene obtained above, 9.1 g (63%) of the expected compound were obtained in the form of a white powder having a melting point of 104°–106° C.

(c) Preparation of Ethyl 3-(3',5'-di-tert-butyl-6-hydroxy-2'-propyloxy-3-biphenylyl)acrylate:

In a manner similar to that of Example 1(c), by reaction of 1.0 g (3.7 mmol) of ethyl 3-(3-bromo-4-hydroxyphenyl)acrylate obtained in Example 34(d) with 2.14 g (7.33 mmol) of 2-propyloxy-3,5-di-tert-butylphenylboronic acid obtained above, 70 mg (4%) of the expected compound were obtained in the form of a colorless oil.

$^1$H NMR (CDCl$_3$): 0.85 (t, J=7.5 Hz, 3H), 1.34 (s, 9H), 1.40 (t, J=7.75 Hz, 3H), 1.45 (s, 9H), 1.55 to 1.59 (m, 2H), 3.43 to 3.65 (m, 2H), 4.27 (q, J=8.25 Hz, 2H), 6.37 (d, J=15.75 Hz, 1H), 7.05 (d, J=8.25 Hz, 1H), 7.16 (d, J=2.5 Hz, 1H), 7.30 (s, 1H), 7.43 (d, J=2.5 Hz, 1H), 7.50 to 7.55 (m, 2H), 7.72 (d, J=16.0 Hz, 1H).

(d) Synthesis of 3-(3',5'-di-tert-Butyl-6-hydroxy-2'-propyloxy-3-biphenylyl)acrylic Acid:

In a manner similar to that of Example 2(h), starting from 70 mg (0.16 mmol) of ethyl 3-(3',5'-di-tert-butyl-6-hydroxy-2'-propyloxy-3-biphenylyl)acrylate obtained above, 50 mg (75%) of the expected compound were obtained in the form of a white powder having a melting point of 187°–189° C.

Example 40

Synthesis of 3-(3',5'-di-tert-Butyl-6-hydroxy-2'-butyloxy-3-biphenylyl)acrylic Acid (a) Preparation of 1-bromo-3,5-di-tert-Butyl-2-butyloxybenzene:

In a manner similar to that of Example 1(a), by reaction of 15 g (52.6 mmol) of 2-bromo-4,6-di-tert-butylphenol with 7.93 g (57.9 mmol) of 1-bromobutane, 17.7 g (100%) of the expected compound were obtained in the form of an orange oil.

$^1$H NMR (CDCl$_3$): 0.99 (t, J=7.5 Hz, 3H), 1.28 (s, 9H), 1.39 (s, 9H), 1.45 to 1.60 (m, 2H), 1.80 to 1.92 (m, 2H), 4.03 (t, J=7.0 Hz, 2H), 7.27 (d, J=2.5 Hz, 1H), 7.39 (d, J=2.5 Hz, 1H).

(b) Preparation of 2-Butyloxy-3,5-di-tert-butylphenylboronic Acid:

In a manner similar to that of Example 1(b), starting from 16.0 g (46.8 mmol) of 1-bromo-3,5-di-tert-butyl-2-butyloxybenzene obtained above, 14 g (97%) of the expected compound were obtained in the form of a white powder having a melting point of 92°–94° C.

(c) Preparation of Ethyl 3-(3',5'-di-tert-Butyl-6-hydroxy-2'-butyloxy-3-biphenylyl)acrylate:

In a manner similar to that of Example 1(c), by reaction of 6.2 g (22.8 mmol) of ethyl 3-(3-bromo-4-hydroxyphenyl) acrylate obtained in Example 34(d) with 14 g (45.7 mmol) of 2-butyloxy-3,5-di-tert-butylphenylboronic acid obtained above, 700 mg (7%) of the expected compound were obtained in the form of a yellow oil.

$^1$H NMR (CDCl$_3$): 0.78 (t, J=7.5 Hz, 3H), 1.31 to 1.56 (m, 25H), 3.20 to 3.66 (m, 2H), 4.27 (q, J=7.25 Hz, 2H), 6.37 (d, J=16.0 Hz, 1H), 7.06 (d, J=8.25 Hz, 1H), 7.16 (d, J=2.5 Hz, 1H), 7.30 (s, 1H), 7.43 (d, J=2.25 Hz, 1H), 7.49 to 7.55 (m, 2H), 7.72 (d, J=16.0 Hz, 1H).

(d) Synthesis of 3-(3',5'-di-tert-Butyl-6-hydroxy-2'-butyloxy-3-biphenylyl)acrylic Acid:

In a manner similar to that of Example 2(h), starting from 430 mg (0.95 mmol) of ethyl 3-(3',5'-di-tert-butyl-6-hydroxy-2'-butyloxy-3-biphenylyl)acrylate obtained above, 300 mg (74%) of the expected compound were obtained in the form of a white powder having a melting point of 194°–196° C.

Example 41

Synthesis of 3-(2'-Butoxy-3',5'-di-tert-butyl-6-methoxy-3-biphenylyl)acrylic Acid (a) Preparation of Ethyl 3-(2'-Butoxy-3',5'-di-tert-butyl-6-methoxy-3-biphenylyl)acrylate:

In a manner similar to that of Example 1(a), by reaction of 230 mg (0.5 mmol) of ethyl 3-(3',5'-di-tert-butyl-6-hydroxy-2'-butyloxy-3-biphenylyl)acrylate obtained in Example 40(c) with 82 mg (0.58 mmol) of iodomethane, 230 mg (100%) of the expected compound were obtained in the form of a yellow oil.

$^1$H NMR (CDCl$_3$): 0.67 (t, J=7.25 Hz, 3H), 1.07 (m, 2H), 1.25 to 1.36 (m, 14H), 1.43 (s, 9H), 3.40 (br, 2H), 3.84 (s, 3H), 4.25 (q, J=7.0 Hz, 2H), 6.33 (d, J=15.5 Hz, 1H), 6.98 (d, J=8.5 Hz, 1H), 7.11 (d, J=2.25 Hz, 1H), 7.35 (d, J=2.5 Hz, 1H), 7.48 (dd, J1=8.5 Hz, J2=2.25 Hz, 1H), 7.56 (d, J=2.25 Hz, 1H), 7.68 (d, J=15.75 Hz, 1H).

(b) Synthesis of 3-(2'-Butoxy-3',5'-di-tert-butyl-6-methoxy-3-biphenylyl)acrylic Acid:

In a manner similar to that of Example 2(h), starting from 230 mg (0.51 mmol) of ethyl 3-(2'-butoxy-3',5'-di-tert-butyl-6-methoxy-3-biphenylyl)acrylate obtained above, 120 mg (55%) of the expected compound were obtained in the form of a white powder having a melting point of 204°–206° C.

Example 42

Synthesis of 3-(3',5'-di-tert-Butyl-6-methoxy-2'-propoxy-3-biphenylyl)acrylic Acid (a) Preparation of Ethyl 3-(3',5'-di-tert-Butyl-6-methoxy-2'-propoxy-3-biphenylyl)acrylate:

In a manner similar to that of Example 1(c), by reaction of 1.0 g (3.5 mmol) of ethyl 3-(3-bromo-4-methoxyphenyl) acrylate obtained in Example 13(d) with 1.54 g (5.26 mmol) of 2-propyloxy-3,5-di-tert-butylphenylboronic acid obtained in Example 39(b), 1.20 g (76%) of the expected compound was obtained in the form of a white powder having a melting point of 107°–109° C.

(b) Synthesis of 3-(3',5'-di-tert-Butyl-6-methoxy-2'-propoxy-3-biphenylyl)acrylic Acid:

In a manner similar to that of Example 2(h), starting from 1.0 g (2.2 mmol) of ethyl 3-(3',5'-di-tert-butyl-6-methoxy-2'-propoxy-3-biphenylyl)acrylate obtained above, 800 mg (85%) of the expected compound were obtained in the form of a white powder having a melting point of 207°–209° C.

Example 43

Synthesis of 3-[4-Hydroxy-3-(5,5,8,8-tetramethyl-4-propoxy-5,6,7,8-tetrahydro-2-naphthyl)phenyl] acrylic Acid (a) Preparation of 3-Bromo-5,5,8,8-tetramethyl-5,6,7,8-tetrahydronaphth-1-ol:

9.73 g (73 mmol) of aluminum chloride were introduced together with 80 ml of dichloromethane under a stream of nitrogen into a 2 liter three-necked flask, and a solution of 25 g (145 mmol) of 3-bromophenol in 100 ml of dichloromethane was added dropwise, and the mixture was stirred at room temperature for 15 minutes. Then a solution of 26.2 g (143 mmol) of 2,5-dichloro-2,5-dimethylhexane in 100 ml of dichloromethane was introduced and the mixture was stirred at room temperature for 1 hour. Then a solution of 40 g (218 mmol) of 2,5-dichloro-2,5-dimethylhexane in 200 ml of dichloromethane was added in four portions with one hour of stirring between each addition and the mixture was stirred for 15 hours. The dichloromethane was evaporated from the reaction medium, the residue was taken up in ethyl acetate and water, and the organic phase was decanted, dried over magnesium sulfate, filtered and evaporated. The residue obtained was purified by chromatography on silica, eluting first with heptane and then with a 95:5 heptane/ethyl acetate mixture. After evaporation of the solvents, 30 g (73%) of the expected compound were obtained in the form of oily black crystals.

$^1$H NMR (CDCl$_3$): 1.25 (s, 6H), 1.38 (s, 6H), 1.58 to 1.67 (m, 4H), 4.99 (s, 1H), 6.25 (d, J=2.0 Hz, 1H), 7.04 (d, J=2.0 Hz, 1H).

(b) Preparation of 2-Bromo-4-propyloxy-5,5,8,8-tetramethyl-5,6,7,8-tetrahydronaphthalene:

In a manner similar to that of Example 1(a), by reaction of 18 g (63.6 mmol) of 3-bromo-5,5,8,8-tetramethyl-5,6,7,8-tetrahydronaphth-1-ol obtained in the preceding example with 8.61 g (70 mmol) of 1-bromopropane, 16.2 g (78%) of the expected compound were obtained in the form of yellow crystals having a melting point of 86°–88° C.

(c) Preparation of 4-Propyloxy-5,5,8,8-tetramethyl-5,6,7,8-tetrahydro-2-naphthylboronic Acid:

In a manner similar to that of Example 1(b), starting from 16.0 g (49.2 mmol) of 2-bromo-4-propyloxy-5,5,8,8-tetramethyl-5,6,7,8-tetrahydronaphthalene obtained above, 6.2 g (46%) of the expected compound were obtained in the form of a white powder having a melting point of 230°–232° C.

(d) Preparation of Ethyl 3-[4-Hydroxy-3-(5,5,8,8-tetramethyl-4-propoxy-5,6,7,8-tetrahydro-2-naphthyl) phenyl]acrylate:

In a manner similar to that of Example 1(c), by reaction of 1.0 g (3.7 mmol) of ethyl 3-(3-bromo-4-hydroxyphenyl) acrylate obtained in Example 34(d) with 1.61 g (5.5 mmol) of 4-propyloxy-5,5,8,8-tetramethyl-5,6,7,8-tetrahydro-2-naphthylboronic acid obtained in Example 43(c), 640 mg (40%) of the expected compound were obtained in the form of a white powder having a melting point of 114°–116° C.

(e) Synthesis of 3-[4-Hydroxy-3-(5,5,8,8-tetramethyl-4-propoxy-5,6,7,8-tetrahydro-2-naphthyl)phenyl]acrylic Acid:

In a manner similar to that of Example 2(h), starting from 640 mg (1.47 mmol) of ethyl 3-[4-hydroxy-3-(5,5,8,8- tetramethyl-4-propoxy-5,6,7,8-tetrahydro-2-naphthyl) phenyl]acrylate obtained above, 270 mg (45%) of the expected compound were obtained in the form of a white powder having a melting point of 209°–211° C.

Example 44

Synthesis of 3-{4-Methoxy-3-[3-benzyloxy-5,5,8,8-tetramethyl-5,6,7,8-tetrahydro-2-naphthyl]phenyl}acrylic Acid (a) Preparation of Ethyl 3-{4-Methoxy-3-[3-benzyloxy-5,5,8,8-tetramethyl-5,6,7,8-tetrahydro-2-naphthyl]phenyl}acrylate:

In a manner similar to that of Example 1(a), by reaction of 1.40 g (3.4 mmol) of ethyl 3-[3-(3-hydroxy-5,5,8,8-tetramethyl-5,6,7,8-tetrahydro-2-naphthyl)-4-methoxyphenyl]acrylate obtained in Example 13(f) with 450 µl (3.77 mmol) of benzyl bromide, 1.64 g (97%) of the expected compound was obtained in the form of a yellow oil.

$^1$H NMR (CDCl$_3$): 1.28 to 1.35 (m, 15H), 1.69 (s, 4H), 3.76 (s, 3H), 4.25 (q, J=7.0 Hz, 2H), 5.02 (s, 2H), 6.30 (d, J=15.75 Hz, 1H), 6.89 (s, 1H), 6.93 (d, J=8.25 Hz, 1H) 7.19 (s, 1H), 7.20 to 7.35 (m, 5H), 7.43 to 7.52 (m, 2H), 7.67 (d, J=16.0 Hz, 1H).

(b) Synthesis of 3-{4-Methoxy-3-[3-benzyloxy-5,5,8,8-tetramethyl-5,6,7,8-tetrahydro-2-naphthyl]phenyl}acrylic Acid:

In a manner similar to that of Example 2(h), starting from 1.64 g (3.3 mmol) of ethyl 3-{4-methoxy-3-[3-benzyloxy-5,5,8,8-tetramethyl-5,6,7,8-tetrahydro-2-naphthyl]phenyl}acrylate obtained above, 1.27 g (82%) of the expected compound were obtained in the form of a white powder having a melting point of 200°–202° C.

Example 45

Synthesis of 3-Methyl-5-[3-(3,5,5,8,8-pentamethyl-5,6,7,8-tetrahydro-2-naphthyl)phenyl]penta-2,4-dienoic Acid (a) Preparation of 3-(3,5,5,8,8-Pentamethyl-5,6,7,8-tetrahydro-2-naphthyl)benzaldehyde:

In a manner similar to that of Example 1(c), by reaction of 2.0 g (8.12 mmol) of 3,5,5,8,8-pentamethyl-5,6,7,8-tetrahydro-2-naphthylboronic acid (prepared in Example 5(a) of the patent WO 97/33881) and 1.89 g (10.15 mmol) of 3-bromobenzaldehyde, 3.10 g (100%) of the expected compound were obtained in the form of a white powder having a melting point of 99°–101° C.

(b) Preparation of Ethyl 3-methyl-5-[3-(3,5,5,8,8-pentamethyl-5,6,7,8-tetrahydro-2-naphthyl)phenyl]penta-2,4-dienoate:

In a manner similar to that of Example 2(c), by reaction of 2.0 g (6.53 mmol) of 3-(3,5,5,8,8-pentamethyl-5,6,7,8-tetrahydro-2-naphthyl)benzaldehyde obtained in the preceding example and 1.90 g (7.20 mmol) of triethyl 3-methyl-4-phosphonocrotonate, 1.80 g (66%) of the expected compound was obtained in the form of a white powder having a melting point of 83°–85° C.

(c) Synthesis of 3-Methyl-5-[3-(3,5,5,8,8-pentamethyl-5,6,7,8-tetrahydro-2-naphthyl)phenyl]penta-2,4-dienoic Acid:

In a manner similar to that of Example 2(h), starting from 1.00 g (2.4 mmol) of ethyl 3-methyl-5-[3-(3,5,5,8,8-pentamethyl-5,6,7,8-tetrahydro-2-naphthyl)phenyl]penta-2,4-dienoate obtained above and after separation of the isomers on a fine silica column (7–35 µm) eluted with a 95:5 heptane/ethyl acetate mixture, 420 mg (45%) of the expected compound were obtained in the form of a white powder having a melting point of 218°–220° C.

B. BIOLOGICAL TEST EXAMPLES

The biological tests carried out correspond to those described above. The results obtained are reported in the following Table:

TABLE

| Compound No. | RXR binding $K_D$ (nM) | RXRα transactivation | |
|---|---|---|---|
| | | Agonist $AC_{50}$ (nM) | Antagonist $IC_{50}$ (nM) |
| 1 | 394 | 384 | — |
| 2 | 23 | inactive | 920 |
| 3 | 10 | inactive | 729 |
| 4 | 17 | 165 | — |
| 5 | 76 | inactive | 4000 |
| 6 | 14 | inactive | 505 |
| 7 | 153 | 32 | — |
| 8 | 235 | inactive | 1100 |
| 9 | 231 | inactive | 631 |

C. EXAMPLES OF SPECIFIC FORMULATIONS BASED ON THE COMPOUNDS OF THE INVENTION (1) ORAL ROUTE:

(a) The following composition was formulated as a 0.8 g tablet:

| | |
|---|---|
| Compound of Example 3 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets are administered to an adult individual per day for 3 to 6 months, depending on the severity of the condition treated.

(b) A drinkable suspension for packaging in 5 ml vials was formulated:

| | |
|---|---|
| Compound of Example 2 | 0.050 g |
| Glycerol | 0.500 g |
| 70% sorbitol | 0.500 g |
| Sodium saccharinate | 0.010 g |
| Methyl parahydroxybenzoate | 0.040 g |
| Flavoring | qs |
| Purified water | qs 5 ml |

For the treatment of acne, 1 vial is administered to an adult individual per day for 3 months, depending on the severity of the condition treated.

(c) The following composition for packaging in gelatin capsules was formulated:

| | |
|---|---|
| Compound of Example 5 | 0.025 g |
| Corn starch | 0.060 g |
| Lactose qs | 0.300 g |

The gelatin capsules comprised gelatin, titanium dioxide and a preservative.

For the treatment of psoriasis, 1 gelatin capsule is administered to an adult individual per day for 30 days.

(2) TOPICAL ROUTE:

(a) The following nonionic water-in-oil cream was formulated:

| | |
|---|---|
| Compound of Example 6 | 0.100 g |
| Mixture of emulsifying lanolin alcohols, waxes and refined oils, marketed by BDF under the trademark "anhydrous Eucerin" | 39.900 g |
| Methyl para-hydroxybenzoate | 0.075 g |
| Propyl para-hydroxybenzoate | 0.075 g |
| Sterile demineralized water qs | 100.000 g |

This cream is applied to psoriatic skin once or twice a day for 30 days.

(b) A gel was formulated from the following composition:

| | |
|---|---|
| Compound of Example 18 | 0.050 g |
| Base erythromycin | 4.000 g |
| Butylhydroxytoluene | 0.050 g |
| Hydroxypropylcellulose marketed by Hercules under the trademark "Klucel HF" | 2.000 g |
| Ethanol (at 95°) qs | 100.000 g |

This gel is applied to skin afflicted with dermatitis or acneic skin 1 to 3 times a day for 6 to 12 weeks, depending on the severity of the condition treated.

(c) An anti-seborrhoeic lotion was formulated by mixing together the following ingredients:

| | |
|---|---|
| Compound of Example 4 | 0.030 g |
| Propylene glycol | 5.000 g |
| Butylhydroxytoluene | 0.100 g |
| Ethanol (at 95°) qs | 100.000 g |

This lotion is applied twice a day to a seborrhoeic scalp, and a significant improvement is observed within a period of between 2 and 6 weeks.

(d) A cosmetic composition to combat the harmful effects of the sun was formulated by mixing together the following ingredients:

| | |
|---|---|
| Compound of Example 25 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Fragrance | 0.400 g |
| Demineralized water qs | 100.000 g |

This composition is applied daily to combat photoinduced skin aging.

(e) The following nonionic oil-in-water cream was formulated:

| | |
|---|---|
| Compound of Example 38 | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

This cream is applied to psoriatic skin once or twice a day for 30 days.

(f) A topical gel was formulated by mixing together the following ingredients:

| | |
|---|---|
| Compound of Example 19 | 0.050 g |
| Ethanol | 43.000 g |
| α-tocopherol | 0.050 g |
| Carboxyvinyl polymer marketed under the trademark "Carbopol 941" by Goodrich | 0.500 g |
| Triethanolamine as an aqueous solution at 20% by weight | 3.800 g |
| Water | 9.300 g |
| Propylene glycol qs | 100.000 g |

This gel is applied in the treatment of acne 1 to 3 times a day for 6 to 12 weeks, depending on the severity of the condition treated.

(g) A hair lotion to combat hair loss and to promote regrowth of the hair was formulated by mixing together the following ingredients:

| | |
|---|---|
| Compound of Example 41 | 0.05 g |
| Compound marketed under the trademark "Minoxidil" | 1.00 g |
| Propylene glycol | 20.00 g |
| Ethanol | 34.92 g |
| Polyethylene glycol (molecular weight = 400) | 40.00 g |
| Butylhydroxyanisole | 0.01 g |
| Butylhydroxytoluene | 0.02 g |
| Water qs | 100.00 g |

This lotion is applied twice a day for 3 months to a scalp which has suffered considerable hair loss.

(h) An anti-acne cream was formulated by mixing together the following ingredients:

| | |
|---|---|
| Compound of Example 13 | 0.050 g |
| Retinoic acid | 0.010 g |
| Mixture of glycerol stearate and polyethylene glycol stearate (75 mol), marketed under the trademark "Gelot 64" by Gattefosse | 15.000 g |
| Kernel oil polyoxyethylenated with 6 mol of ethylene oxide, marketed under the trademark "Labrafil M2130 CS" by Gattefosse | 8.000 g |
| Perhydrosqualene | 10.000 g |
| Preservatives | qs |
| Polyethylene glycol (molecular | 8.000 g |

| | |
|---|---|
| weight = 400) | |
| Disodium salt of ethylenediamine-tetraacetic acid | 0.050 g |
| Purified water qs | 100.000 g |

This cream is applied to skin afflicted with dermatitis or to acneic skin 1 to 3 times a day for 6 to 12 weeks.

(i) An oil-in-water cream was formulated from the following composition:

| | |
|---|---|
| Compound of Example 29 | 0.020 g |
| Betamethasone 17-valerate | 0.050 g |
| S-Carboxymethylcysteine | 3.000 g |
| Polyoxyethylene stearate (40 mol of ethylene oxide) marketed under the trademark "Myrj 52" by Atlas | 4.000 g |
| Sorbitan monolaurate, polyoxyethylene with 20 mol of ethylene oxide, marketed under the trademark "Tween 20" by Atlas | 1.800 g |
| Mixture of glyceryl mono- and distearate marketed under the trademark "Geleol" by Gattefosse | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preservatives | qs |
| Perhydrosqualene | 18.000 g |
| Mixture of caprylic/capric triglycerides marketed under the trademark "Miglyol 812" by Dynamit Nobel | 4.000 g |
| Triethanolamine (99% by weight) | 2.500 g |
| Water qs | 100.000 g |

This cream is applied twice a day to skin afflicted with dermatitis, for 30 days.

(j) The following oil-in-water cream was formulated:

| | |
|---|---|
| Lactic acid | 5.000 g |
| Compound of Example 33 | 0.020 g |
| Polyoxyethylene stearate (40 mol of ethylene oxide) marketed under the trademark "Myrj 52" by Atlas | 4.000 g |
| Sorbitan monolaurate, polyoxyethylene with 20 mol of ethylene oxide, marketed under the trademark "Tween 20" by Atlas | 1.800 g |
| Mixture of glyceryl mono- and distearate marketed under the trademark "Geleol" by Gattefosse | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preservatives | qs |
| Perhydrosqualene | 18.000 g |
| Mixture of caprylic/capric triglycerides marketed under the trademark "Miglyol 812" by Dynamit Nobel | 4.000 g |
| Water qs | 100.000 g |

This cream is applied once a day to combat aging, whether photoinduced or chronological aging.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A bicyclic aromatic compound having the structural formula (I):

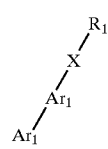

in which $R_1$ is (i) the radical $-CH_3$, (ii) a radical $-CH_2OR_2$, or (iii) a radical $-CO-R_3$, wherein $R_2$ and $R_3$ are as defined below; $Ar_1$ is a radical selected from among those of the following formulae (a)–(c):

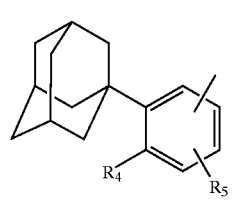

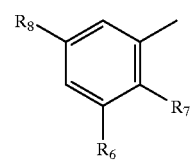

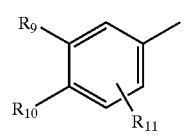

wherein $R_4$, $R_5$, $R_6$, $R_7$, $R_8$, $R_9$, $R_{10}$ and $R_{11}$ are as defined below; $Ar_2$ is a radical selected from among those of the following formulae (d)–(h):

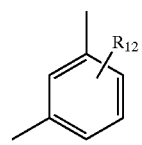

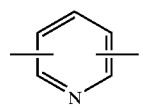

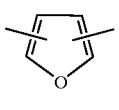

-continued

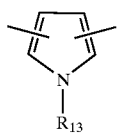
(h)

wherein $R_{12}$ and $R_{13}$ are as defined below; X is a radical selected from among those of the following formulae (i)–(l):

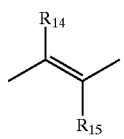
(i)

(j)

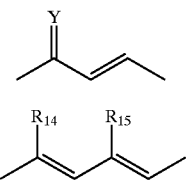
(k)

(l)

wherein $R_{14}$, $R_{15}$ and Y are as defined below; $R_2$ is a hydrogen atom, a lower alkyl radical or a radical —CO—$R_{16}$, wherein $R_{16}$ is as defined below; $R_3$ is a hydrogen atom, a lower alkyl radical, a radical of the formula:

wherein R' and R" are as defined below, or a radical —$OR_{17}$, wherein $R_{17}$ is as defined below; $R_4$ is a hydrogen atom, a polyether radical, a lower alkyl radical, or a radical —$OR_{18}$, wherein $R_{18}$ is as defined below; $R_5$ is a hydrogen atom, a lower alkyl radical, a polyether radical, or a radical —$OR_{19}$, wherein $R_{19}$ is as defined below; $R_6$ is a tert-butyl radical; $R_7$ is a lower alkyl radical, a polyether radical, or a radical —$OR_{20}$, wherein $R_{20}$ is as defined below, with the proviso that $R_6$ and $R_7$ may together form, with the carbon atoms from which they depend, a 6-membered ring optionally substituted with at least one methyl group and/or optionally interrupted by an oxygen or sulfur atom; $R_8$ is a tert-butyl, adamantyl, aryl or aralkyl radical; $R_9$ and $R_{10}$ together form, with the carbon atoms from which they depend, a 5- or 6-membered ring optionally substituted with at least one methyl group and/or optionally interrupted by an oxygen or sulfur atom; $R_{11}$ is a hydrogen atom, a lower alkyl radical having from 1 to 9 carbon atoms, a hydroxyl radical, an alkoxy radical, a polyether radical or a radical —$OR_{21}$, wherein $R_{21}$ is as defined below; $R_{12}$ is a hydrogen atom, a hydroxyl radical, an alkoxy radical, a polyether radical or a radical —$OR_{22}$, wherein $R_{22}$ is as defined below; $R_{13}$ is a hydrogen atom, a lower alkyl radical, or a radical —$COR_{23}$, wherein $R_{23}$ is as defined below; $R_{14}$ and $R_{15}$, which may be identical or different, are each a hydrogen atom, or a lower alkyl radical; Y is an oxygen atom or a $CH_2$ radical; $R_{16}$ is a lower alkyl radical; $R_{17}$ is a hydrogen atom, a linear or branched alkyl radical having from 1 to 20 carbon atoms, an alkenyl radical, a mono- or polyhydroxyalkyl radical, an optionally substituted aryl or aralkyl radical or a sugar residue; R' and R", which may be identical or different, are each a hydrogen atom, a lower alkyl radical, a mono- or polyhydroxyalkyl radical, an optionally substituted aryl radical or an amino acid residue, with the proviso that R' and R" may together form, with the nitrogen atom from which they depend, a nitrogenous heterocycle; $R_{18}$, $R_{19}$ and $R_{20}$, which may be identical or different, are each a hydrogen atom, a lower alkyl radical, an alkenyl radical, a mono- or polyhydroxyalkyl radical, an aryl radical, an optionally substituted aralkyl radical or a radical —$(CH_2)_n$—$R_{24}$, wherein n and $R_{24}$ are as defined below; $R_{21}$ and $R_{22}$, which may be identical or different, are each an alkenyl radical, a mono- or polyhydroxyalkyl radical, an aryl radical, an optionally substituted aralkyl radical, or a radical —$(CH_2)_n$—$R_{24}$, wherein n and $R_{24}$ are as defined below; $R_{23}$ is a lower alkyl radical; $R_{24}$ is a heterocycle, a monohydroxyalkyl radical, a thiol radical optionally substituted with a lower alkyl radical, an amino radical optionally substituted with at least one lower alkyl radical, a radical —$COOR_{25}$, or a radical —$CON(R_{26})R_{27}$, wherein $R_{25}$, $R_{26}$ and $R_{27}$ are as defined below; $R_{25}$ is a hydrogen atom or a lower alkyl radical; $R_{26}$ and $R_{27}$, which may be identical or different, are each a hydrogen atom, a lower alkyl radical, or an optionally substituted aryl radical, with the proviso that $R_{26}$ and $R_{27}$ may together form, with the nitrogen atom from which they depend, a nitrogenous heterocycle; n is an integer such that $2 \leq n \leq 9$; with the further provisos that, when $Ar_1$ is the radical of formula (c) and X is a radical of formulae (i) or (j), then $R_{11}$ is a radical —$OR_{21}$ or a polyether radical, or when $Ar_2$ is the radical of formula (d), then $R_{12}$ is a radical —$OR_{22}$ or a polyether radical, and the compounds of formula (I) do not include those wherein $R_{11}$ is a methoxymethoxy radical in an ortho position relative to the substituent $Ar_2$ when $Ar_1$ is the radical of formula (c), X is the radical of formula (i), $R_{12}$ is hydrogen and $R_1$ is a radical —$COR_3$ wherein $R_3$ is a radical —$OR_{17}$ and $R_{17}$ is a hydrogen atom, and those wherein $R_{12}$ is a methoxymethoxy radical in an ortho- or para-position relative to the substituent $Ar_1$ when $Ar_1$ is the radical of formula (c), X is the radical of formula (i), $R_{11}$ is a methyl radical in an ortho-position relative to $Ar_2$, and $R_1$ is a radical —$COR_3$ wherein $R_3$ is a radical —$OR_{17}$ and $R_{17}$ is a hydrogen atom; and the pharmaceutically/cosmetically acceptable optical and geometric isomers and salts thereof, wherein said compound is an RXR antagonist.

2. A bicyclic aromatic compound as defined by claim 1, wherein formula (I), $Ar_1$ is a radical having the formula (a).

3. A bicyclic aromatic compound as defined by claim 1, wherein formula (I), $Ar_1$ is a radical having the formula (b).

4. A bicyclic aromatic compound as defined by claim 1, wherein formula (I), $Ar_1$ is a radical having the formula (c).

5. A bicyclic aromatic compound as defined by any of claims 2–4, wherein formula (I), $Ar_2$ is a radical having the formula (d).

6. A bicyclic aromatic compound as defined by any of claims 2–4, wherein formula (I), $Ar_2$ is a radical having the formula (e).

7. A bicyclic aromatic compound as defined by any of claims 2–4, wherein formula (I), $Ar_2$ is a radical having the formula (f).

8. A bicyclic aromatic compound as defined by any of claims 2–4, wherein formula (I), $Ar_2$ is a radical having the formula (g).

9. A bicyclic aromatic compound as defined by any of claims 2–4, wherein formula (I), $Ar_2$ is a radical having the formula (h).

10. A bicyclic aromatic compound as defined by claim 5, wherein formula (I), X is a radical (i).

11. A bicyclic aromatic compound as defined by claim 6, wherein formula (I), X is a radical (j).

12. A bicyclic aromatic compound as defined by claim 7, wherein formula (I), X is a radical (k).

13. A bicyclic aromatic compound as defined by claim 8, wherein formula (I), X is a radical (l).

14. A bicyclic aromatic compound as defined by claim 1, comprising a pharmaceutically/cosmetically acceptable salt thereof.

15. A bicyclic aromatic compound as defined by claim 1, wherein formula (I), $R_1$ is a radical —CO—$R_3$; $Ar_1$ is a radical of formulae (d) or (e); $R_{11}$ is a radical —O—$R_{21}$; and $R_7$ is a radical —O—$R_{20}$.

16. A bicyclic aromatic compound as defined by claim 1, having the formula (I) and containing at least one lower alkyl radical substituent selected from among methyl, ethyl, isopropyl, butyl, tert-butyl and hexyl radicals.

17. A bicyclic aromatic compound as defined by claim 1, having the formula (I) and containing at least one monohydroxyalkyl radical substituent selected from among 2-hydroxyethyl, 2-hydroxypropyl and 3-hydroxypropyl radicals.

18. A bicyclic aromatic compound as defined by claim 1, having the formula (I) and containing at least one polyhydroxyalkyl radical substituent selected from among 2,3-dihydroxypropyl, 2,3,4-trihydroxybutyl, 2,3,4,5-tetrahydroxypentyl and pentaerythritol radicals.

19. A bicyclic aromatic compound as defined by claim 1, having the formula (I) and containing at least one aryl radical substituent selected from among phenyl radicals optionally substituted by at least one halogen atom, or at least one lower alkyl, alkoxy, polyether, optionally protected amino, hydroxyl or nitro group.

20. A bicyclic aromatic compound as defined by claim 1, having the formula (I) and containing at least one aralkyl radical substituent selected from among benzyl and phenethyl radicals optionally substituted by at least one halogen atom, or at least one lower alkyl, alkoxy, polyether, optionally protected amino, hydroxyl or nitro group.

21. A bicyclic aromatic compound as defined by claim 1, having the formula (I) and containing at least one sugar residue substituent selected from among those of glucose, galactose, mannose and glucuronic acid.

22. A bicyclic aromatic compound as defined by claim 1, having the formula (I) and containing at least one amino acid residue substituent selected from among those of lysine, glycine and aspartic acid.

23. A bicyclic aromatic compound as defined by claim 1, having the formula (I) and containing at least one heterocyclic radical substituent selected from among piperidino, morpholino, pyrrolidino and piperazino radicals which are optionally substituted by a $C_1$–$C_6$ alkyl radical or a mono- or polyhydroxyalkyl radical.

24. A bicyclic aromatic compound as defined by claim 1, having the formula (I) and containing at least one alkenyl radical substituent having from 2 to 5 carbon atoms and one or more sites of ethylenic unsaturation.

25. A bicyclic aromatic compound as defined by claim 1, having the formula (I) and containing at least one polyether radical substituent selected from among methoxymethyl ether, methoxyethoxymethyl ether and methylthiomethyl ether radicals.

26. A pharmaceutical composition of matter, comprising a therapeutically effective amount of a bicyclic aromatic compound as defined by claim 1, or pharmaceutically acceptable salt or isomer thereof, and a pharmaceutically acceptable carrier, diluent or vehicle therefor.

27. The pharmaceutical composition as defined by claim 26, further comprising a retinoid compound, a D vitamin or derivative thereof, a corticosteriod, an anti-free radical agent, an antioxidant, an $\alpha$-hydroxy or $\alpha$-keto acid or derivative thereof, an ion channel blocker, or combination thereof.

28. The pharmaceutical composition as defined by claim 26, comprising a tablet, a capsule, a syrup, a suspension, an elixir, a solution, a powder, granules, an emulsion, microspheres, nanospheres, lipid vesicles, polymeric vesicles, or an injectable.

29. The pharmaceutical composition as defined by claim 26, comprising an ointment, a cream, a milk, a pommade, a salve, an impregnated pad, a gel, a spray, or a lotion.

30. The pharmaceutical composition as defined by claim 26, adopted for topical administration.

31. The pharmaceutical composition as defined by claim 26, adopted for systemic administration.

32. The pharmaceutical composition as defined by claim 26, comprising from 0.001% to 5% by weight of said bicyclic aromatic compound, or salt or isomer thereof.

33. A regime/regimen for treating a keratinization disorder in a mammalian organism in need of such treatment, comprising administering to such organism a therapeutically effective amount of the pharmaceutical composition as defined by claim 26.

34. A regime/regimen for treating a dermatological disorder in a mammalian organism in need of such treatment, comprising administering to such organism a therapeutically effective amount of the pharmaceutical composition as defined by claim 26.

35. A regime/regimen for treating an ophthalmological disorder in a mammalian organism in need of such treatment, comprising administering to such organism a therapeutically effective amount of the pharmaceutical composition as defined in claim 26.

36. A regime/regimen for treating skin aging in a mammalian organism in need of such treatment, comprising administering to such organism a therapeutically effective amount of the pharmaceutical composition as defined in claim 26.

37. A regime/regimen for treating epidermal and/or dermal atrophy in a mammalian organism in need of such treatment, comprising administering to such organism a therapeutically effective amount of the pharmaceutical composition as defined by claim 26.

38. A regime/regimen for treating a cicatrization disorder in a mammalian organism in need of such treatment, comprising administering to such organism a therapeutically effective amount of the pharmaceutical composition as defined in claim 26.

39. A regime/regimen for treating a sebaceous function disorder in a mammalian organism in need of such treatment, comprising administering to such organism a therapeutically effective amount of the pharmaceutical composition as defined by claim 26.

40. A regime/regimen for treating a cancerous or precancerous disease state in a mammalian organism in need of such treatment, comprising administering to such organism a therapeutically effective amount of the pharmaceutical composition as defined by claim 26.

41. A regime/regimen for treating inflammation in a mammalian organism in need of such treatment, comprising administering to such organism a therapeutically effective amount of the pharmaceutical composition as defined by claim 26.

42. A regime/regimen for treating a viral infection in a mammalian organism in need of such treatment, comprising administering to such organism a therapeutically effective amount of the pharmaceutical composition as defined by claim 26.

43. A regime/regimen for treating or preventing alopecia in a mammalian organism in need of such treatment, comprising administering to such organism a therapeutically effective amount of the pharmaceutical composition as defined by claim 26.

44. A regime/regimen for treating a cardiovascular disorder in a mammalian organism in need of such treatment, comprising administering to such organism a therapeutically effective amount of the pharmaceutical composition as defined by claim 26.

45. A regime/regimen for treating an immune deficiency in a mammalian organism in need of such treatment, comprising administering to such organism a therapeutically effective amount of the pharmaceutical composition as defined by claim 26.

46. A regime/regimen for treating a dermatological, rheumatic, respiratory, cardiovascular or ophthalmologic disorder in a mammalian organism in need of such treatment, comprising administering to such organism a therapeutically effective amount of the pharmaceutical composition as defined by claim 26.

47. A regime/regimen as defined by claim 46, comprising administering to such organism a daily dose of said bicyclic aromatic compound of about 0.01 mg/kg to 100 mg/kg of body weight thereof.

48. A cosmetic composition of matter, comprising a cosmetically effective amount of a bicyclic aromatic compound as defined by claim 1, or cosmetically acceptable salt or isomer thereof, and a cosmetically acceptable carrier, diluent or vehicle therefor.

49. The cosmetic composition as defined by claim 46, comprising a cream, a milk, a lotion, a gel, microspheres, nanospheres, lipid vesicles, polymeric vesicles, a soap, or a shampoo.

50. The cosmetic composition as defined by claim 48, comprising from 0.001% to 3% by weight or said bicyclic aromatic compound, or salt or isomer thereof.

51. The cosmetic composition as defined by claim 48, further comprising a retinoid compound, a D vitamin or derivative thereof, a corticosteroid, an anti-free radical agent, an antioxidant, an $\alpha$-hydroxy, or $\alpha$-keto acid or derivative thereof, an ion channel blocker, or combination thereof.

52. A regime/regimen for treating a skin or hair disorder on a mammalian organism in need of such treatment, comprising administering to such organism a cosmetically/therapeutically effective amount of the cosmetic composition as defined by claim 48.

53. The pharmaceutical composition as defined by claim 26, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

54. The pharmaceutical composition as defined by claim 26, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

55. The cosmetic composition by claim 48, further comprising a wetting agent, a depigmenting agent, a moisturizing agent, an antiseborrhoic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

56. The cosmetic composition as defined by claim 49, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *